(12) United States Patent
Royer et al.

(10) Patent No.: US 10,993,669 B2
(45) Date of Patent: May 4, 2021

(54) ANCHORING SYSTEM FOR A CATHETER DELIVERED DEVICE

(71) Applicant: ENDOTRONIX, INC., Lisle, IL (US)

(72) Inventors: Trace Royer, Chicago, IL (US); Tyler Panian, Naperville, IL (US); David Schaller, Winfield, IL (US); Omid Forouzan, Chicago, IL (US); Tom Wilschke, Chicago, IL (US)

(73) Assignee: ENDOTRONIX, INC., Lisle, IL (US)

( * ) Notice: Subject to any disclaimer, the term of this patent is extended or adjusted under 35 U.S.C. 154(b) by 0 days.

(21) Appl. No.: 15/958,613

(22) Filed: Apr. 20, 2018

(65) Prior Publication Data
US 2018/0303426 A1    Oct. 25, 2018

Related U.S. Application Data

(60) Provisional application No. 62/487,508, filed on Apr. 20, 2017, provisional application No. 62/624,146, filed on Jan. 31, 2018.

(51) Int. Cl.
*A61B 5/00* (2006.01)
*A61M 25/04* (2006.01)
(Continued)

(52) U.S. Cl.
CPC .......... *A61B 5/6882* (2013.01); *A61B 5/0031* (2013.01); *A61B 5/6876* (2013.01);
(Continued)

(58) Field of Classification Search
CPC ... A61B 5/6882; A61B 5/0215; A61B 5/0031; A61B 5/6876; A61B 5/6884;
(Continued)

(56) References Cited

U.S. PATENT DOCUMENTS 3,714,595 A    1/1973 Denenberg et al.
3,872,455 A    3/1975 Fuller et al.
(Continued)

FOREIGN PATENT DOCUMENTS

CN    1701464    11/2005
CN    101116322    1/2008
(Continued)

OTHER PUBLICATIONS

International Search Report of PCT/US2018/028580, Endotronix, Inc., Sep. 2018. (Year: 2018).*

(Continued)

*Primary Examiner* — Paul B Prebilic
(74) *Attorney, Agent, or Firm* — McDonald Hopkins LLC

(57) ABSTRACT

The present disclosure relates to various anchoring systems for a catheter delivered device. In one instance the anchoring systems of the present disclosure are designed to be used in connection with a pulmonary artery implant device. In one embodiment, an anchoring system of the present disclosure comprises two anchoring ends, a distal end anchoring structure and a proximal end anchoring structure, where at least one of the distal or proximal anchoring structures has a clover-shaped structure formed by at least three lobes. In another embodiment, the distal anchoring structure includes an elongated and angled shape formed by wire material. In another embodiment, both the distal and proximal anchoring structures have a clover-shaped structure formed by at least three lobes.

30 Claims, 12 Drawing Sheets

(51) Int. Cl.
*A61M 25/01* (2006.01)
*A61M 25/02* (2006.01)
*A61B 5/0215* (2006.01)

(52) U.S. Cl.
CPC ............ *A61B 5/6884* (2013.01); *A61M 25/01* (2013.01); *A61M 25/04* (2013.01); *A61B 5/0215* (2013.01); *A61M 2025/0293* (2013.01)

(58) Field of Classification Search
CPC ........ A61B 2560/04; A61B 2560/0406; A61B 2560/06; A61B 2560/063; A61B 2560/066; A61M 25/01; A61M 25/04; A61M 2025/0293; A61M 2205/04
See application file for complete search history.

(56) References Cited

U.S. PATENT DOCUMENTS

| | | |
|---|---|---|
| 3,888,708 A | 6/1975 | Wise et al. |
| 3,943,915 A | 3/1976 | Severson |
| 4,023,562 A | 5/1977 | Hynecek et al. |
| 4,026,276 A | 5/1977 | Chubbuck |
| 4,037,324 A | 7/1977 | Andreasen |
| 4,067,235 A | 1/1978 | Markland et al. |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson et al. |
| 4,511,858 A | 4/1985 | Charavit et al. |
| 4,531,526 A | 7/1985 | Genest |
| 4,543,955 A | 10/1985 | Schroeppel |
| 4,567,459 A | 1/1986 | Folger et al. |
| 4,644,420 A | 2/1987 | Buchan |
| 4,815,472 A | 3/1989 | Wise et al. |
| 4,881,410 A | 11/1989 | Wise et al. |
| 4,953,387 A | 9/1990 | Johnson et al. |
| 4,966,034 A | 10/1990 | Bock et al. |
| 5,005,577 A | 4/1991 | Frenkel |
| 5,006,819 A | 4/1991 | Buchan et al. |
| 5,013,396 A | 5/1991 | Wise et al. |
| 5,046,497 A | 9/1991 | Millar |
| 5,055,838 A | 10/1991 | Wise et al. |
| 5,058,581 A | 10/1991 | Silvian |
| 5,059,543 A | 10/1991 | Wise et al. |
| 5,108,420 A | 4/1992 | Marks |
| 5,113,868 A | 5/1992 | Wise et al. |
| 5,227,798 A | 7/1993 | Hildebrand |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |
| 5,334,952 A | 8/1994 | Maddy et al. |
| 5,343,064 A | 8/1994 | Spangler et al. |
| 5,368,040 A | 11/1994 | Carney |
| 5,377,524 A | 1/1995 | Wise et al. |
| 5,417,235 A | 5/1995 | Wise et al. |
| 5,510,276 A | 4/1996 | Diem et al. |
| 5,564,434 A | 10/1996 | Halperin et al. |
| 5,581,248 A | 12/1996 | Spillman, Jr. et al. |
| 5,690,674 A | 11/1997 | Diaz |
| 5,840,148 A | 11/1998 | Campbell |
| 5,872,520 A | 2/1999 | Seifert et al. |
| 5,873,835 A | 2/1999 | Hastings |
| 5,920,233 A | 7/1999 | Denny |
| 5,938,602 A | 8/1999 | LLoyd |
| 5,992,769 A | 11/1999 | Wise et al. |
| 6,015,386 A | 1/2000 | Kensey et al. |
| 6,025,725 A | 2/2000 | Gershenfeld et al. |
| 6,109,113 A | 8/2000 | Chavan et al. |
| 6,111,520 A | 8/2000 | Allen et al. |
| 6,126,675 A | 10/2000 | Shchervinsky et al. |
| 6,140,144 A | 10/2000 | Najafi et al. |
| 6,174,322 B1 | 1/2001 | Schneidt |
| 6,190,400 B1 | 2/2001 | Van De Moer et al. |
| 6,206,835 B1 | 3/2001 | Spillman, Jr. et al. |
| 6,232,150 B1 | 5/2001 | Lin et al. |
| 6,278,379 B1 | 8/2001 | Allen et al. |
| 6,287,256 B1 | 9/2001 | Park et al. |
| 6,309,350 B1 | 10/2001 | VanTassel et al. |
| 6,331,163 B1 | 12/2001 | Kaplan |
| 6,338,284 B1 | 1/2002 | Najafi et al. |
| 6,359,444 B1 | 3/2002 | Grimes |
| 6,366,804 B1 | 4/2002 | Mejia |
| 6,438,408 B1 | 8/2002 | Mulligan et al. |
| 6,447,449 B1 | 9/2002 | Fleischman et al. |
| 6,454,720 B1 | 9/2002 | Clerc et al. |
| 6,459,253 B1 | 10/2002 | Krusell |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fischer et al. |
| 6,636,769 B2 * | 10/2003 | Govari ............... A61B 5/0031 |
| | | 128/903 |
| 6,645,143 B2 | 11/2003 | VanTassel et al. |
| 6,647,778 B2 | 11/2003 | Sparks |
| 6,658,300 B2 | 12/2003 | Govari et al. |
| 6,661,294 B2 | 12/2003 | Terashima et al. |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,699,186 B1 | 3/2004 | Wolinsky et al. |
| 6,713,828 B1 | 3/2004 | Chavan et al. |
| 6,749,622 B2 | 6/2004 | McGuckin, Jr. et al. |
| 6,764,446 B2 | 7/2004 | Wolinsky et al. |
| 6,766,200 B2 | 7/2004 | Cox |
| 6,779,406 B1 | 8/2004 | Kuzina et al. |
| 6,783,499 B2 * | 8/2004 | Schwartz ............ A61B 5/0031 |
| | | 128/898 |
| 6,805,667 B2 | 10/2004 | Christopherson et al. |
| 6,817,983 B1 | 11/2004 | Millar |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,923,625 B2 | 8/2005 | Sparks |
| 6,926,670 B2 | 8/2005 | Rich et al. |
| 6,932,114 B2 | 8/2005 | Sparks |
| 6,935,010 B2 | 8/2005 | Tadigadpa et al. |
| 6,939,299 B1 | 9/2005 | Peterson et al. |
| 6,945,939 B2 | 9/2005 | Turcott |
| 6,959,608 B2 | 11/2005 | Bly et al. |
| 6,968,743 B2 | 11/2005 | Rich et al. |
| 6,970,742 B2 | 11/2005 | Mann et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,007,551 B2 | 3/2006 | Zdeblick et al. |
| 7,013,734 B2 | 3/2006 | Zdeblick et al. |
| 7,025,727 B2 | 4/2006 | Brockway et al. |
| 7,028,550 B2 | 4/2006 | Zdeblick et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |
| 7,096,068 B2 | 8/2006 | Mass et al. |
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,174,212 B1 | 2/2007 | Klehn et al. |
| 7,181,261 B2 | 2/2007 | Silver et al. |
| 7,192,001 B2 | 3/2007 | Wise et al. |
| 7,198,603 B2 | 4/2007 | Penner et al. |
| 7,200,439 B2 | 4/2007 | Zdeblick et al. |
| 7,211,048 B1 | 5/2007 | Najafi et al. |
| 7,228,735 B2 | 6/2007 | Sparks et al. |
| 7,229,415 B2 | 6/2007 | Schwartz |
| 7,236,821 B2 | 6/2007 | Cates et al. |

(56) References Cited

U.S. PATENT DOCUMENTS

| | | |
|---|---|---|
| 7,245,117 B1 | 7/2007 | Joy et al. |
| 7,273,457 B2 | 9/2007 | Penner |
| 7,274,965 B1 | 9/2007 | Karicheria et al. |
| 7,284,442 B2 | 10/2007 | Fleischman et al. |
| 7,290,454 B2 | 11/2007 | Liu |
| 7,321,337 B2 | 1/2008 | Ikeda et al. |
| 7,335,161 B2 | 2/2008 | Von Arx et al. |
| 7,425,200 B2 | 9/2008 | Brockway et al. |
| 7,432,723 B2 | 10/2008 | Ellis et al. |
| 7,439,723 B2 | 10/2008 | Allen et al. |
| 7,452,334 B2 | 11/2008 | Gianchandani et al. |
| 7,466,120 B2 | 12/2008 | Miller et al. |
| 7,481,771 B2 | 1/2009 | Fonseca et al. |
| 7,483,743 B2 | 1/2009 | Mann et al. |
| 7,483,805 B2 | 1/2009 | Sparks et al. |
| 7,492,144 B2 | 2/2009 | Powers et al. |
| 7,498,799 B2 | 3/2009 | Allen et al. |
| 7,509,169 B2 | 3/2009 | Eigler et al. |
| 7,532,933 B2 | 5/2009 | Hastings et al. |
| 7,550,978 B2 | 6/2009 | Joy et al. |
| 7,566,308 B2 | 7/2009 | Stahmann |
| 7,572,226 B2 | 8/2009 | Scheiner et al. |
| 7,572,228 B2 | 8/2009 | Wolinksy et al. |
| 7,574,792 B2 | 8/2009 | O'Brien et al. |
| 7,621,036 B2 | 11/2009 | Cros |
| 7,641,619 B2 | 1/2010 | Penner |
| 7,645,233 B2 | 1/2010 | Tulkki et al. |
| 7,647,831 B2 | 1/2010 | Corcoran et al. |
| 7,662,653 B2 | 2/2010 | O'Brien et al. |
| 7,678,132 B2 | 3/2010 | Abbott et al. |
| 7,678,135 B2 | 3/2010 | Maahs et al. |
| 7,679,355 B2 | 3/2010 | Allen et al. |
| 7,682,313 B2 | 3/2010 | Bodecker et al. |
| 7,686,762 B1 | 3/2010 | Najafi et al. |
| 7,686,768 B2 | 3/2010 | Bodecker et al. |
| 7,686,828 B2 | 3/2010 | Abbott et al. |
| 7,699,059 B2 | 4/2010 | Fonseca et al. |
| 7,708,705 B2 | 5/2010 | Iddan et al. |
| 7,737,301 B2 | 6/2010 | Walter et al. |
| 7,742,815 B2 | 6/2010 | Salo et al. |
| 7,790,493 B2 | 9/2010 | Wise et al. |
| 7,792,588 B2 | 9/2010 | Harding |
| 7,801,613 B2 | 9/2010 | Li et al. |
| 7,839,153 B2 | 11/2010 | Joy et al. |
| 7,860,579 B2 | 12/2010 | Goetzinger et al. |
| 7,890,186 B2 | 2/2011 | Wardle et al. |
| 7,899,550 B1 | 3/2011 | Doan et al. |
| 7,931,671 B2 | 4/2011 | Tenerz |
| 7,932,732 B2 | 4/2011 | Joy et al. |
| 7,936,174 B2 | 5/2011 | Ellis et al. |
| 7,945,333 B2 | 5/2011 | Jacobson |
| 7,953,496 B2 | 5/2011 | Cole |
| 8,014,865 B2 | 9/2011 | Najafi et al. |
| 8,021,307 B2 | 9/2011 | White |
| 8,025,625 B2 | 9/2011 | Allen |
| 8,083,767 B2 | 12/2011 | Modesitt |
| 8,093,991 B2 | 1/2012 | Stevenson et al. |
| 8,103,361 B2 | 1/2012 | Moser |
| 8,118,749 B2 | 2/2012 | White |
| 8,154,389 B2 | 4/2012 | Rowland et al. |
| 8,241,325 B2 | 8/2012 | Modesitt |
| 8,267,863 B2 | 9/2012 | Najafi et al. |
| 8,267,954 B2 | 9/2012 | Decant, Jr. et al. |
| 8,271,093 B2 | 9/2012 | Von Arx et al. |
| 8,303,511 B2 | 11/2012 | Eigler et al. |
| 8,308,794 B2 | 11/2012 | Martinson et al. |
| 8,323,192 B2 | 12/2012 | Kilcoyne et al. |
| 8,353,841 B2 | 1/2013 | White |
| 8,355,777 B2 | 1/2013 | White |
| 8,360,984 B2 | 1/2013 | Yadav |
| 8,432,265 B2 | 4/2013 | Rowland et al. |
| 8,493,187 B2 | 7/2013 | Rowland et al. |
| 8,512,252 B2 | 8/2013 | Ludomirsky et al. |
| 8,570,186 B2 | 10/2013 | Nagy et al. |
| 8,630,702 B2 | 1/2014 | Fischell et al. |
| 8,852,099 B2 | 10/2014 | Von Arx et al. |
| 9,060,696 B2 | 6/2015 | Eigler et al. |
| 9,572,982 B2 | 2/2017 | Burnes et al. |
| 9,616,223 B2 | 4/2017 | Schugt et al. |
| 9,867,552 B2 | 1/2018 | Rowland et al. |
| 2002/0111662 A1 | 8/2002 | Iaizzo |
| 2003/0125790 A1* | 7/2003 | Fastovsky ............ A61B 5/0215 623/1.11 |
| 2006/0064036 A1 | 3/2006 | Osborne |
| 2008/0071178 A1* | 3/2008 | Greenland ........... A61B 5/0031 600/486 |
| 2008/0071339 A1 | 3/2008 | Stalker |
| 2008/0176271 A1* | 7/2008 | Silver ................. A61B 5/0031 435/29 |
| 2012/0046560 A1* | 2/2012 | White ................. A61B 5/0215 600/486 |
| 2012/0296222 A1* | 11/2012 | Griswold ............ A61B 5/6876 600/486 |
| 2013/0253347 A1* | 9/2013 | Griswold ........... A61N 1/37205 600/486 |
| 2015/0208929 A1* | 7/2015 | Rowland ........... A61M 25/0662 600/486 |
| 2016/0002995 A1 | 1/2016 | Naedler et al. |

FOREIGN PATENT DOCUMENTS

| | | |
|---|---|---|
| HK | 1147906 | 8/2011 |
| JP | 2000-005136 | 1/2000 |
| JP | 2000-517073 | 12/2000 |
| JP | 2002-515278 | 5/2002 |
| JP | 2003-144417 | 5/2003 |
| JP | 2005-284511 | 10/2005 |
| JP | 2006-512112 | 4/2006 |
| JP | 2006-309582 | 11/2006 |
| JP | 2007-210547 | 8/2007 |
| JP | 2007-256287 | 10/2007 |
| JP | 2008-022935 | 2/2008 |
| JP | 2008-532590 | 8/2008 |
| JP | 2010-538254 | 12/2010 |
| WO | 2004/045407 | 6/2004 |
| WO | 2005/018507 | 3/2005 |
| WO | 2005/107583 | 11/2005 |
| WO | 2006/070278 | 7/2006 |
| WO | 2006/096582 | 9/2006 |
| WO | 2006/130488 | 12/2006 |
| WO | 2008/091409 | 7/2008 |
| WO | 2008/098255 | 8/2008 |
| WO | 2008/115456 | 9/2008 |
| WO | 2008/137703 | 11/2008 |
| WO | 2009/146089 | 12/2009 |
| WO | 2010117356 | 10/2010 |
| WO | 2010117597 | 10/2010 |
| WO | 2012/015955 | 2/2012 |
| WO | WO-2013081660 A1 * | 6/2013 ........... A61B 5/0215 |
| WO | 2014070316 | 5/2014 |
| WO | WO-2014070316 A1 * | 5/2014 ........... A61B 5/0022 |

OTHER PUBLICATIONS

International Preliminary Examination Report of PCT/US2018/028580, Endotronix, Inc. Oct. 2019. (Year: 2019).*

Patent Cooperation Treaty, International Search Report for PCT/US/2018/028580, dated Sep. 12, 2018, 19 pages.

Extended European Search Report for application EP13850155.6, PCT/US2013/059769, dated Apr. 19, 2016, European Patent Office, Germany.

Patent Cooperation Treaty (PCT), International Search Report and Written Opinion for application PCT/US2013/059769, dated Dec. 13, 2013, International Searching Authority, US.

Patent Cooperation Treaty (PCT), International Search Report and Written Opinion for application PCT/US2011/045583, dated Nov. 23, 2011, International Searching Authority, NL.

Extended European Search Report for application EP12804636.4, PCT/2012044998, dated Jan. 20, 2015, European Patent Office, Germany.

AU Patent Examination Report No. 1 for application AU2012275126, dated Apr. 9, 2016, Australian Government IP Australia, Australia.

(56) References Cited

OTHER PUBLICATIONS

Patent Cooperation Treaty (PCT), International Search Report and Written Opinion for application PCT/US2010/27951, dated Aug. 25, 2010, International Searching Authority, US.
Patent Cooperation Treaty (PCT), Written Opinion of the International Searching Authority for application PCT/US2008/03475, dated Aug. 4, 2008, International Searching Authority, US.
Patent Cooperation Treaty (PCT), International Search Report and Written Opinion for application PCT/US2012/44998, dated Sep. 25, 2012, International Searching Authority, US.
Patent Cooperation Treaty (PCT), International Search Report and Written Opinion for application PCT/US2011/045581, dated Oct. 18, 2011, International Searching Authority, US.
Patent Cooperation Treaty (PCT), International Search Report and Written Opinion for application PCT/US2008/69229, dated Oct. 1, 2008, International Searching Authority, US.
AU Patent Examination Report No. 1 for application AU2010235020, dated Aug. 18, 2014, Australian Government IP Australia, Australia.
CA Examination Report for application CA2757952, PCT/US2010/027951, dated Oct. 28, 2015, Canadian Intellectual Property Office, Canada.
Extended European Search Report for application EP10762085.8, PCT/2010027951, dated Jan. 4, 2013, European Patent Office, Germany.
International Preliminary Report on Patentability, Endotronix, Inc. PCT/US2012/034979, dated Nov. 7, 2013.
Patent Cooperation Treaty (PCT), Written Opinion of the International Searching Authority for application PCT/US2009/39730, dated Jun. 30, 2009, International Searching Authority, US.
Communication pursuant to Article 94(3) EPC from the European Patent Office; Application No. 10 762 085.8-1660; dated Jan. 26, 2015.
International Preliminary Report on Patentability, Nunez, Anthony, I. et al. PCT/US2008/003475, dated Sep. 24, 2009.
Communication pursuant to Article 94(3) EPC from the European Patent Office; Application No. 10 762 085.8-1660; dated Sep. 17, 2015.
PK Examination Report for application PK189/2011, emailed Jun. 6, 2013, Pakistan Patent Office, Pakistan.
Collins, Carter, Miniature Passive Pressure Transensor for Implanting in the Eye, Transactions on Bio-Medical Engineering, vol., BME-14, No. 2, pp. 74-83, Apr. 1967.
Nagumo, Uchiyama A., Kimoto, S., Watanuki, T., Hori, M., Suma, K., Ouchi, A., Kumano, M. and Watanabe, H., Echo Capsule for Medical Use (A Batteryless Endoradiosonde), IRE Transaction on Bio-Medical Electronics, pp. 196-199; Feb. 1, 1962.

* cited by examiner

ANCHORING SYSTEM FOR A CATHETER DELIVERED DEVICE

CROSS-REFERENCE TO RELATED APPLICATIONS

This application claims priority to and benefit of U.S. Provisional Application No. 62/487,508 entitled "ANCHORING SYSTEM FOR A CATHETER DELIVERED DEVICE," filed on Apr. 20, 2017, which is hereby incorporated by reference in its entirety. This application also claims priority to and benefit of U.S. Provisional Application No. 62/624,146 entitled "DEVICE AND METHOD FOR DEPLOYING AND SECURING AN IMPLANT TO A VESSEL WALL," filed on Jan. 31, 2018, which is also related to U.S. patent application Ser. No. 14/428,551 entitled "PRESSURE SENSOR, ANCHOR, DELIVERY SYSTEM AND METHOD" filed on Mar. 16, 2015 which claims priority to PCT Patent Application No. PCT/US2013/059769 entitled "PRESSURE SENSOR, ANCHOR, DELIVERY SYSTEM AND METHOD" filed on Sep. 13, 2013 which claims priority to Provisional Patent Application No. 61/701,058 entitled "PRESSURE SENSOR, ANCHOR, DELIVERY SYSTEM AND METHOD," filed on Sep. 14, 2012, each of which are hereby incorporated by reference in their entirety.

FIELD OF THE DISCLOSURE

The present disclosure relates to various anchoring systems for a catheter delivered device. In one instance the anchoring systems of the present disclosure are designed to be used in connection with an implant, such as a pulmonary artery implant device. In one embodiment, an anchoring system of the present disclosure comprises two anchoring ends, a distal end anchoring structure and a proximal end anchoring structure, where at least one of the distal or proximal anchoring structures has a clover-shaped structure formed by at least three lobes. In another embodiment, the distal end anchoring structure has an elongated and angled orientation relative the implant body. In another embodiment, both the distal and proximal anchoring structures have a clover-shaped structure formed by at least three lobes.

BACKGROUND

Recently, the long-sought goal of implantable biosensors has begun to see realization and, thus, clinical use. As this use for implantable biosensors has developed and grown, issues regarding intracorporeal fixation of the sensor have come to light. Particularly within blood vessels, the sensor is subjected to a continuous, pulsatile flow. This is a difficult environment in which to secure a sensor or other apparatus reliably without unduly restricting blood flow and/or impairing the vessel wall. Further, some devices require accurate positioning within the body in order to achieve sufficient wireless communication with a device outside the body. One major vessel of interest in the realm of cardiology is the pulmonary artery. The pulmonary artery is a particularly challenging location in which to secure an intracorporeal device because, in addition to the above considerations, the vessel is especially thin, compliant and prone to perforation.

Implantable wireless sensors are useful in assisting diagnosis and treatment of many diseases. Some of these sensors may be configured to communicate with wireless sensor readers. Examples of wireless sensor readers are disclosed in U.S. Pat. Nos. 8,154,389, 8,493,187, and 8,570,186 and each are incorporated by reference herein. In particular, there are many applications where measuring pressure from within a blood vessel deep in a patient's body is desired. For example, measuring the pressure in the heart's pulmonary artery is helpful in optimizing treatment of heart failure and pulmonary hypertension. In this type of application, an implant may need to be positioned up to 20 cm beneath the surface of the skin. These devices may require a specific implant to provide optimal functionality of the reader/sensor system. An optimal implant for such systems may be configured to transduce pressure into an electrical resonant frequency. Examples of these implants are described in U.S. Pat. No. 9,867,552 entitled "IMPLANTABLE SENSOR ENCLOSURE WITH THIN SIDEWALLS," and U.S. Utility Ser. No. 14/777,654 entitled "PRESSURE SENSING IMPLANT," each of which are hereby incorporated by reference herein in their entirety.

Design considerations for an ideal fixation device intended for intravascular fixation are outlined as follows. The fixation device should be passive and maintain a separation distance between the sensor and the vessel wall. Alternatively, the fixation device may be placed against a vessel wall in a particular geometric arrangement for sensing and communication. The implant should have secure attachment against a smooth, slippery surface in the presence of continuous pulsatile flow. The implant should be able to adapt and conform to a compliant surface which may be undergoing radial distention and contraction. The deployed size and radial strength of the device should be sufficient to prevent its migration into vessels that would be occluded by the dimensions of the sensor while creating minimal stress concentrations where the fixation device contacts the vessel wall. Alternatively, intracorporeal devices should be designed sufficiently small in size so that when deployed in organs or regions with sufficiently redundant blood flow, the device can embolize on its own without harming the organ or the host. Finally, the fixation device should be sufficiently versatile as not to depend, within physiologically relevant ranges, on the size of the vessel in order to maintain its position. The implant should be sufficiently versatile to accommodate a broad range of vessel sizes, curves, random sub-branches, and tortuosity. Otherwise, unintended proximal movement or dislodgement of the fixation device may pose serious health risks that may require surgical intervention.

The implant should meet these requirements without damaging or puncturing delicate vessel walls, or without translating, rotating, or becoming dislodged and migrating to a different location in the vessel. Anchors for the implant must also be foldable in order to be placed within the vessel with a catheter in a minimally invasive procedure. This is a difficult environment in which to secure an implant or other apparatus reliably without unduly restricting blood flow and/or impairing the vessel wall.

There have been various attempts to create devices intended to hold intracorporeal devices fixedly within vessels. Known implants and anchoring assemblies have not always been successful in balancing the tradeoff between establishing a secure anchor against the vessel wall at an intended location while maintaining vessel safety and integrity. Several such attempts are described in U.S. Pat. No. 8,021,307. The anchors disclosed therein use the super elastic properties of nitinol. They do not need to be expanded with a balloon or utilize a transition temperature above room temperature. As such, the anchors of U.S. Pat. No. 8,021,307 intend to position their implantable device centrally within the vessel lumen. However, given the design utilized in U.S.

Pat. No. 8,021,307, the anchors disclosed therein rely on passive placement within a vessel and have a longitudinally extending configuration. These designs have a very limited intended vessel size range in which the device may be stable. Since the overall size of the anchors is also very small, the device is intended to be placed in a very distal and small section of the pulmonary artery—the location of which may vary greatly from patient to patient. At this distal location, the pulmonary artery is extremely delicate and wireless communication must be performed from the patients back. As such, the anchors of U.S. Pat. No. 8,021,307 utilize a very low outward radial force as to not damage the distal pulmonary artery vessel in which they are indicated for. This lack of outward radial force results in a poor stability and thus an increased chance of device rotation and migration both acutely and chronically.

Further, it is a challenge for health clinicians to position the implant in a desired location within the vessel of a patient particularly when the location is tied to an allowable vessel size range. Many times it becomes necessary to utilize a CT scan or "quantitative angiography" to make precise measurements of vessel sizes and configurations with the help of software. These methods require special equipment, added time, and operator skill which may often not be available.

Thus, acute placement and long term stability of an implantable device in a blood vessel is a challenging task. The environment is dynamic and extremely sensitive to disturbances. As such, there are many design considerations associated with fixating the sensor or implant within a blood vessel. One consideration is for the sensor and anchoring assembly to be apposed to a specific side of the vessel wall for the safety of the patient and the performance and functionality of the device. In other words, a given implantable device should land where it is intended to land with reduced subsequent rotation or migration. The device should remain stable when exposed to pulsatile blood flow, the changing diameter of a compliant vessel, changing pressures, and several other physiological factors. The device should not exert force that could damage or perforate the vessel wall and it also should not substantially disturb normal blood flow. Finally, the device should remain stable over a diverse range of patient vessel shapes and sizes without clinically disrupting the vasculature. Any variation of these design factors may interrupt electronic communication with the implantable device, cause grave health consequences, or otherwise fail.

Given the above, there is a need in the art for both an improved implant and anchoring system and method of utilizing the same to deliver an implantable device into a blood vessel such as a pulmonary blood vessel. The instant disclosure provides an anchor assembly design that is intended to address the above identified problems.

SUMMARY

The present disclosure relates to various anchoring assemblies and systems for a catheter delivered device. In one instance the anchoring systems of the present disclosure are designed to be used in connection with a pulmonary artery implant device. In one embodiment, an anchoring system of the present disclosure comprises two anchoring ends, a distal end anchoring structure and a proximal end anchoring structure, where at least one of the distal or proximal anchoring structures has a clover-shaped structure formed by at least three lobes. In another embodiment, the distal end anchoring structure has an elongated and angled orientation relative the implant body. In another embodiment, both the distal and proximal anchoring structures have a clover-shaped structure formed by at least three lobes.

In one embodiment, the present disclosure relates to an anchoring system for a biomedical sensor comprising: a biomedical sensor having a distal end and a proximal end; and an anchoring system comprising a distal anchor and a proximal anchor, where the distal anchor is attached to the distal end of the biomedical sensor and the proximal anchor is attached to the proximal end of the biomedical sensor, wherein at least one of the distal anchor or the proximal anchor has formed therein at least three lobe structures arranged in a manner where at least two smaller lobes are located on either side of a larger lobe so as to accomplish secure placement of the biomedical sensor upon implantation thereof by a catheter device.

In one embodiment, provided is an anchoring assembly for a vascular implant comprising an implant including an oblong shaped housing that extends along a housing axis. At least one anchor may be attached to said housing. Said at least one anchor may be formed from at least one flexible member configured to be placed into a retracted position for catheter delivery and placed in an expanded position for placement within a vessel. Said at least one anchor may be configured to position said housing against a vessel wall. The at least one anchor may be configured to adapt to at least one anatomical feature of a vessel to prevent movement of said housing. The at least one anchor may be a distal anchor attached to a distal end of said implant or the at least one anchor may be a proximal anchor attached to a proximal end of said housing. Further, the implant may include two anchors wherein one anchor is a proximal anchor attached to a proximal end of said housing and the other anchor is a distal anchor attached to a distal end of said housing. The at least one anchor may be a wire and the wire may be made of at least one type of material selected from the following: nitinol, stainless steel, platinum, polished nitinol, low-inclusion nitinol, nitinol with a platinum core, and polymer.

The at least one anatomical feature may be a first vessel segment oriented at an angle with respect to an adjoining second vessel segment. The first vessel segment may be the right interlobar pulmonary artery and said second vessel segment may be the right posterior basal pulmonary artery. The housing may be configured to be located in said first vessel segment, and said at least one anchor may be configured to extend into said second vessel segment a distance sufficient to prevent translational movement of said implant in at least one direction by impeding movement of the implant about said angle formed by said vessel segments. The housing of said implant may be configured to be located in said first vessel segment, and said at least one anchor is configured to extend into said second vessel segment a distance sufficient to prevent rotational movement of said implant by inhibiting movement of said implant about said housing axis. The housing may be configured to be positioned at a location near the surface of the skin and the housing may be configured to communicate wirelessly with a device positioned outside said vessel containing said implant.

The assembly may be configured to facilitate deployment of said vascular implant at a predetermined location wherein said predetermined location is identifiable by proximity to at least one anatomical feature. Said at least one anatomical feature may be an intersection of the superior apical branch and the interlobar branch of the right pulmonary artery. The anchor configured to extend into said second vessel segment may be a distal anchor located on the distal portion of said housing. A proximal anchor may be configured to hold said housing against said wall of said vessel. Said anchor may include a base portion and an elongated portion wherein said elongated portion extends along an elongated axis, wherein said elongated axis extends at a desired angular orientation relative to said second vessel segment. The anchor may include at least three lobe structures arranged in a manner where at least two smaller lobes are located on either side of a larger lobe. Said implant may be a sensor or may be an actuator. Said actuator may be selected from among the following: neurostimulation, cardiac pacing, electrical stimulation, drug elution.

In another embodiment, the present disclosure relates to an anchoring system for a biomedical sensor comprising: a biomedical sensor having a distal end and a proximal end; and an anchoring system comprising a distal anchor and a proximal anchor, where the distal anchor is attached to the distal end of the biomedical sensor and the proximal anchor is attached to the proximal end of the biomedical sensor, wherein both the distal anchor and the proximal anchor have formed therein at least three lobe structures arranged in a manner where at least two smaller lobes are located on either side of a larger lobe so as to accomplish secure placement of the biomedical sensor upon implantation thereof by a catheter device.

In another embodiment, provided is a method for anchoring an implant inside a blood vessel. The steps comprises: attaching at least one flexible anchor to a housing, the housing extends along a housing axis. Said anchor may be collapsed to a collapsed configuration and said housing may be attached to a catheter. The catheter may be inserted into a vasculature system and said housing may be translated to a deployment location. The housing may be released from the catheter and the at least one anchor may be caused to expand thereby disconnecting said housing from said catheter, wherein said anchor positions said housing against a wall of said vessel, further wherein said at least one anchor adapts to at least one anatomical feature to inhibit movement of said housing. The catheter may be removed. Said anchor may be an elongated and angled anchor. Said at least one anchor may include at least three lobe structures arranged in a manner where at least two smaller lobes are located on either side of a larger lobe. Said at least one anchor may be formed from a nitinol alloy. Said housing may include a sensor that is designed for use in a pulmonary artery and said sensor may be designed to be read wirelessly from the chest of a patient in which said sensor is implanted.

In another embodiment, the present disclosure relates to a method for inserting a biomedical sensor and anchoring system for securing same, the method comprising the steps of: (i) placing a biomedical sensor-anchoring system combination into an insertion catheter where the biomedical sensor-anchoring system combination comprises: a biomedical sensor having a distal end and a proximal end; and an anchoring system comprising a distal anchor and a proximal anchor, where the distal anchor is attached to the distal end of the biomedical sensor and the proximal anchor is attached to the proximal end of the biomedical sensor, wherein at least one of the distal anchor or the proximal anchor has formed therein at least three lobe structures arranged in a manner where at least two smaller lobes are located on either side of a larger lobe so as to accomplish secure placement of the biomedical sensor upon implantation thereof by an insertion catheter; (ii) inserting the insertion catheter with the biomedical sensor-anchoring system combination into a desired blood vessel; and (iii) implanting the biomedical sensor-anchoring system combination into a desired blood vessel by releasing the biomedical sensor-anchoring system combination from the insertion catheter such that anchoring system secures placement of the biomedical sensor in a desired location in the desired blood vessel.

DETAILED DESCRIPTION

The present disclosure relates to various anchoring systems for a catheter delivered device. In one instance the anchoring systems of the present disclosure are designed to be used in connection with a pulmonary artery implant device. In one embodiment, an anchoring system of the present disclosure comprises two anchoring ends, a distal end anchoring structure and a proximal end anchoring structure, where at least one of the distal or proximal anchoring structures has a clover-shaped structure formed by at least three lobes. In another embodiment, the distal end anchoring structure has an elongated and angled orientation relative the implant body. In another embodiment, both the distal and proximal anchoring structures have a clover-shaped structure formed by at least three lobes.

Figure 1:
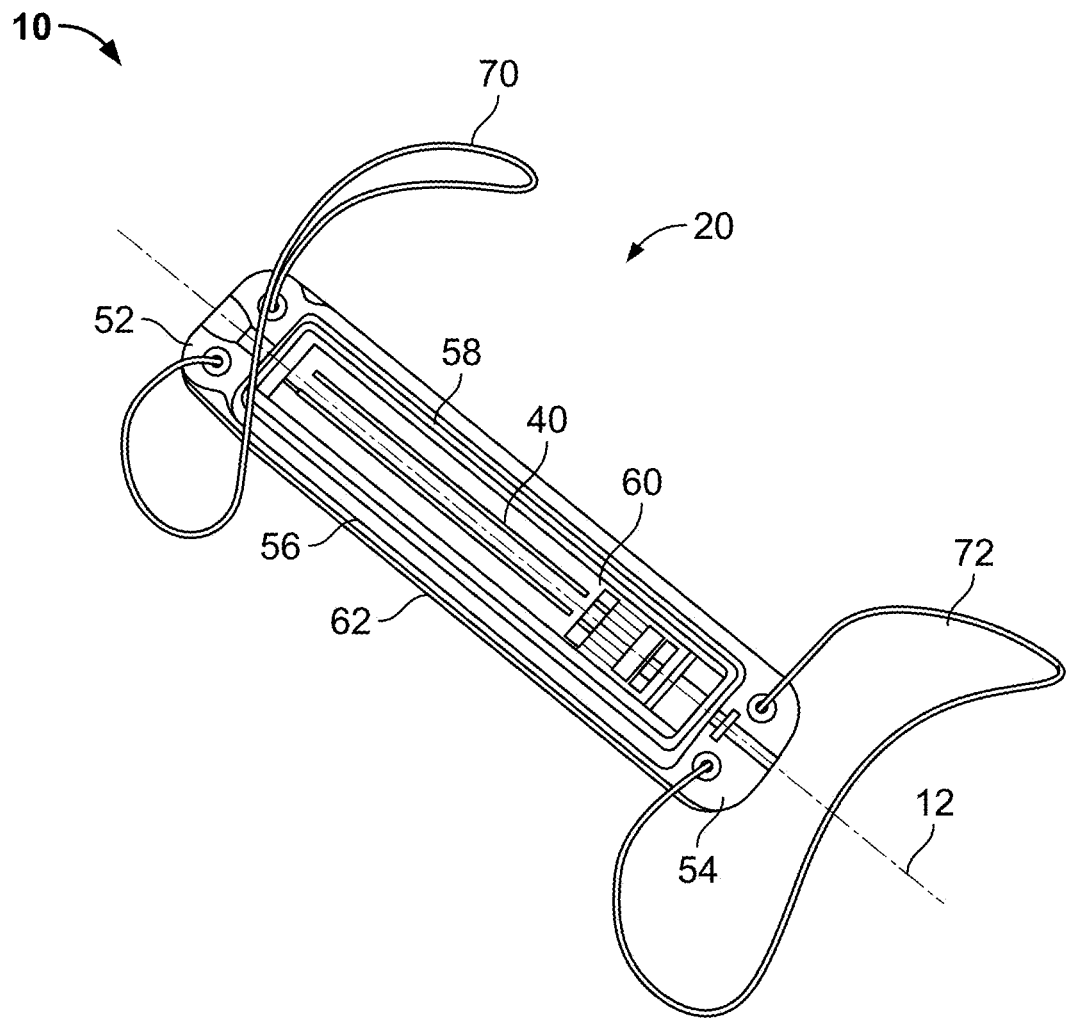
FIG. 1 is a perspective view of a known implant.

FIG. 1 illustrates a prior art implant 10 that includes a housing 20 that includes an oblong, narrow, rectangular shape that extends along a housing axis 12, although the housing may have various shapes and geometry. The dimension of the housing 20 may be generally cuboid and may define a cavity therein. The housing side walls may be of specific dimensions and proportions to each other. For example, the housing may have four side walls 52, 54, 56, and 58, a top wall 60 and a bottom wall 62. The housing 20 may be made of a hermetic, strong, and biocompatible material, such as ceramic. The examples illustrate a cuboid housing, but other shapes and configurations may be used, such as cylindrical housings, prism-shaped housings, octagonal or hexagonal cross-sectioned housings, or the like. A sensor 40 is positioned along the top wall 60 and is attached to an antenna coil as well as other electronic components that may be positioned within the housing of the implant. The sensor 40 as well as the antenna coil and internal electronics may be positioned along a sensor axis 42 that extends generally normal relative to the implant 10 wherein the sensor 40 along the top surface 60 may be exposed to blood flow and pressure within the vessel once positioned within a patient. A distal anchor 70 and a proximal anchor 72 opposite the distal anchor may extend from the top surface of the implant 10. The anchors may fixate the implant 10 in a desired position in the body of the patient.

Figure 2:
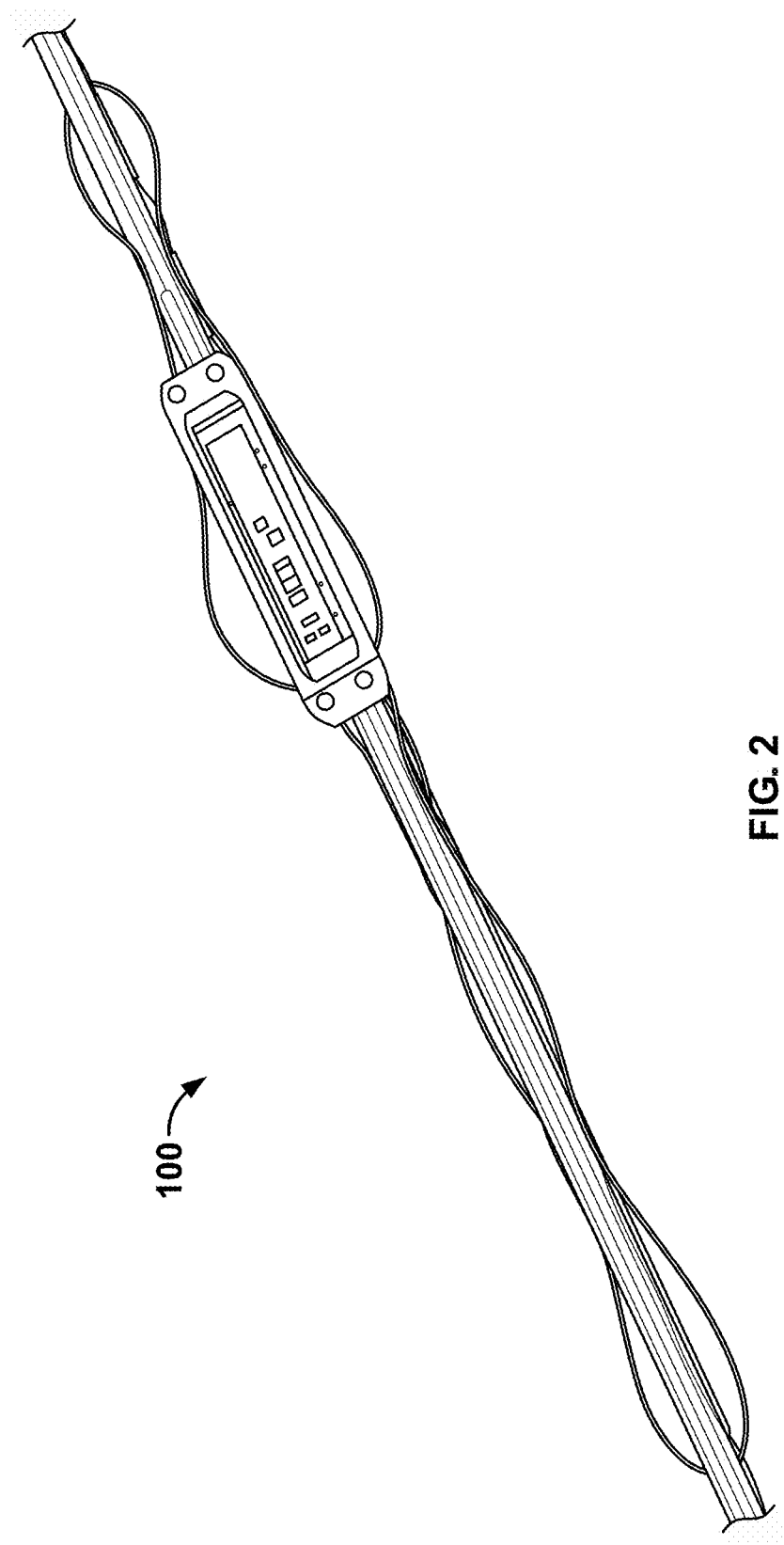
FIG. 2 is a photographic illustration of a sensor device or implant and an anchoring structure according to an embodiment of the present disclosure in a state ready for insertion into a patient and/or individual.

FIGS. 2-10 disclose various embodiments of an anchoring system according to the present disclosure. FIG. 2 depicts an embodiment of an anchoring assembly 100 of the present disclosure in a state ready for insertion into a patient and/or individual by, for example, a catheter in a minimally invasive procedure.

Figure 3A:
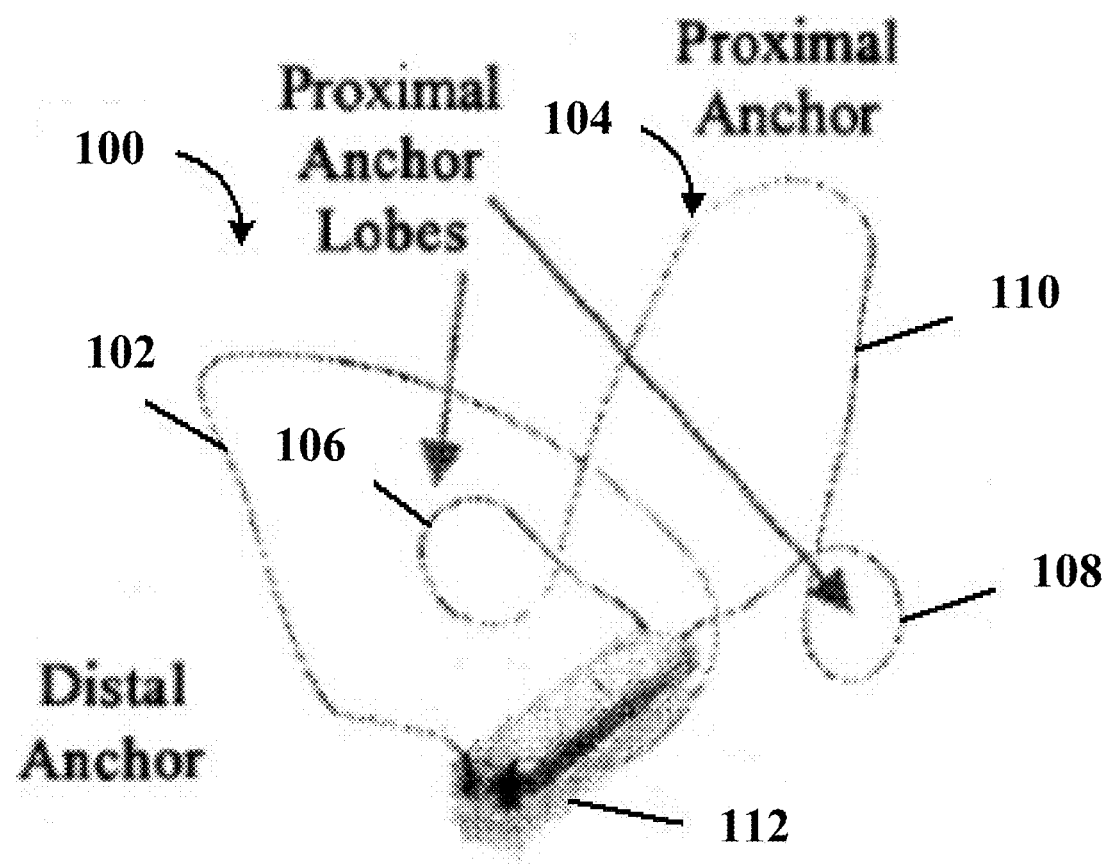
FIG. 3A is a photographic illustration of an embodiment of a sensor device or implant and an anchoring structure attached thereto in a state where the anchoring structure is in its expanded state as would be the case once placement occurs in a desired blood vessel (e.g., a pulmonary blood vessel)
Figure 3B:
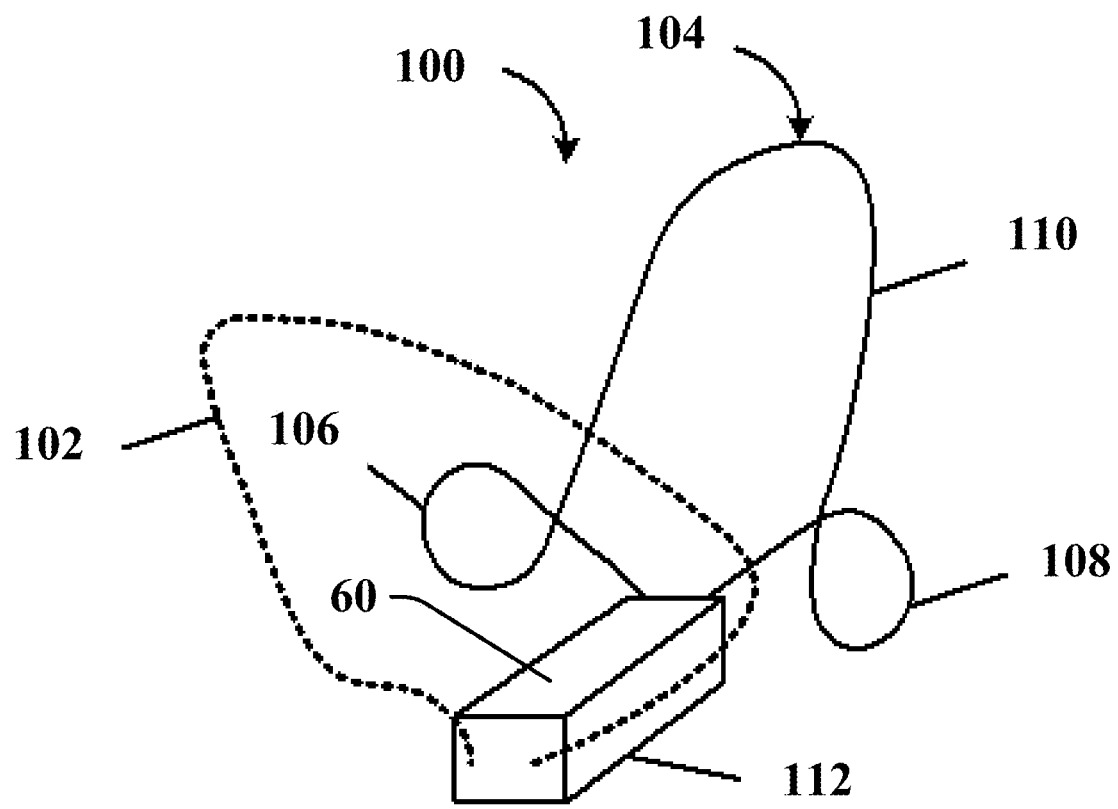
FIG. 3B is a schematic illustration of an embodiment of a sensor device or implant and an anchoring structure attached thereto in a state where the anchoring structure is in an expanded state as would be the case once placement occurs in a desired blood vessel (e.g., a pulmonary blood vessel)
Figure 4:
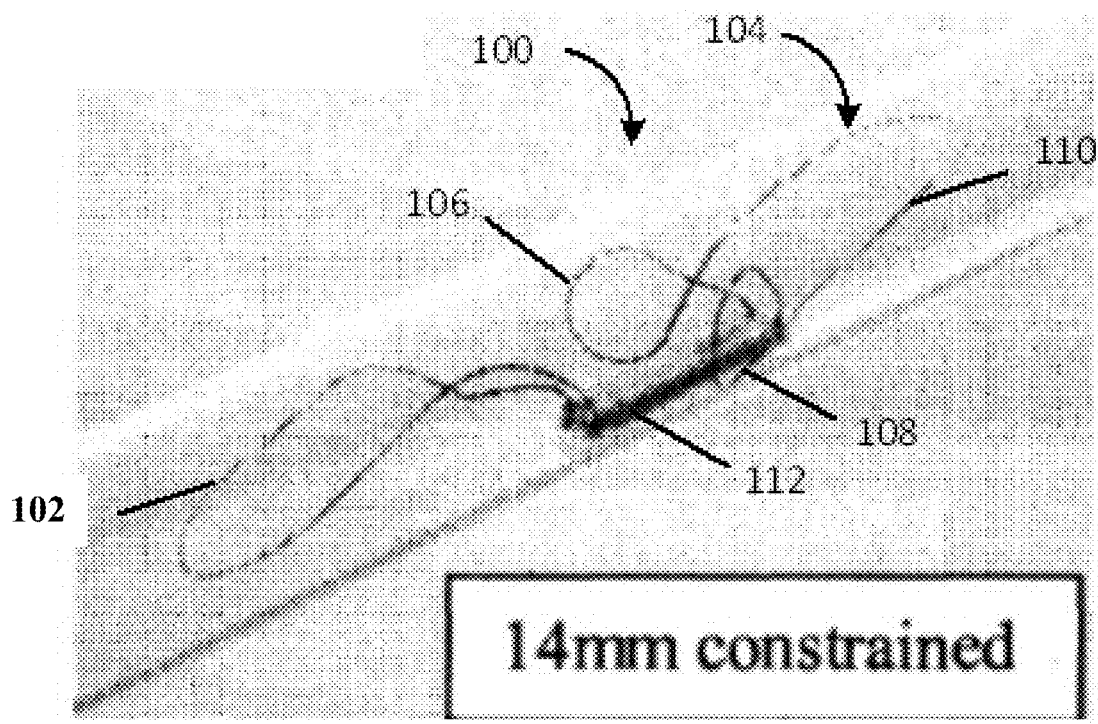
FIG. 4 is a photographic illustration of a sensor device or implant and an anchoring structure attached thereto in a state where the anchoring structure is in an expanded state in a 14 mm blood vessel (e.g., a pulmonary blood vessel)

As illustrated by the embodiments in FIGS. 3A-3B, the anchoring assembly 100 comprises two anchoring ends, a distal anchoring structure 102 and a proximal anchoring structure 104, where at least one of the distal or proximal anchoring structures 102/104 has a clover-shaped structure formed by at least smaller two lobes 106 and 108 located on either side of a larger lobe 110. Located in between the distal anchoring structure 102 and the proximal anchoring structure 104 is a suitable implant sensor 112, such as the implant 10 illustrated by FIG. 1. FIG. 4 depicts the present invention in a state where the anchoring structure is in an expanded state in a 14 mm blood vessel, e.g., a pulmonary blood vessel.

The distal anchoring structure 102 and the proximal anchoring structure 104 may extend from a top surface 60 of the implant 10. Notably, the top surface 60 may include a sensor 40 as illustrated by FIG. 1. Alternatively, the implant 10 may include an actuator such as one that may be selected from among the following: neurostimulation, cardiac pacing, electrical stimulation, drug elution and the embodiments of the implant and anchoring system is not limited as to the type of sensor that may be utilized. Furthermore, the anchoring structures may comprise two individual shape set nitinol wires. As illustrated by FIGS. 3A-3B, the two wires comprise a distal wire and a proximal wire, where one anchor wire 102 is attached to the distal portion of a top surface 60 (spade shape, see FIGS. 3A-3B) of the implant 112 and the other anchor wire 104 is attached to the proximal portion of the top surface 60 (club shape, see FIGS. 3A-3B). Both anchors 102/104 can be collapsed down and attached to a delivery catheter via "release wires" or other mechanism like a shroud. The implant 112 and anchors 102/104 can be introduced into the human vasculature in the collapsed position and expanded to place the implant within a desired location of a vessel.

Figure 5A:
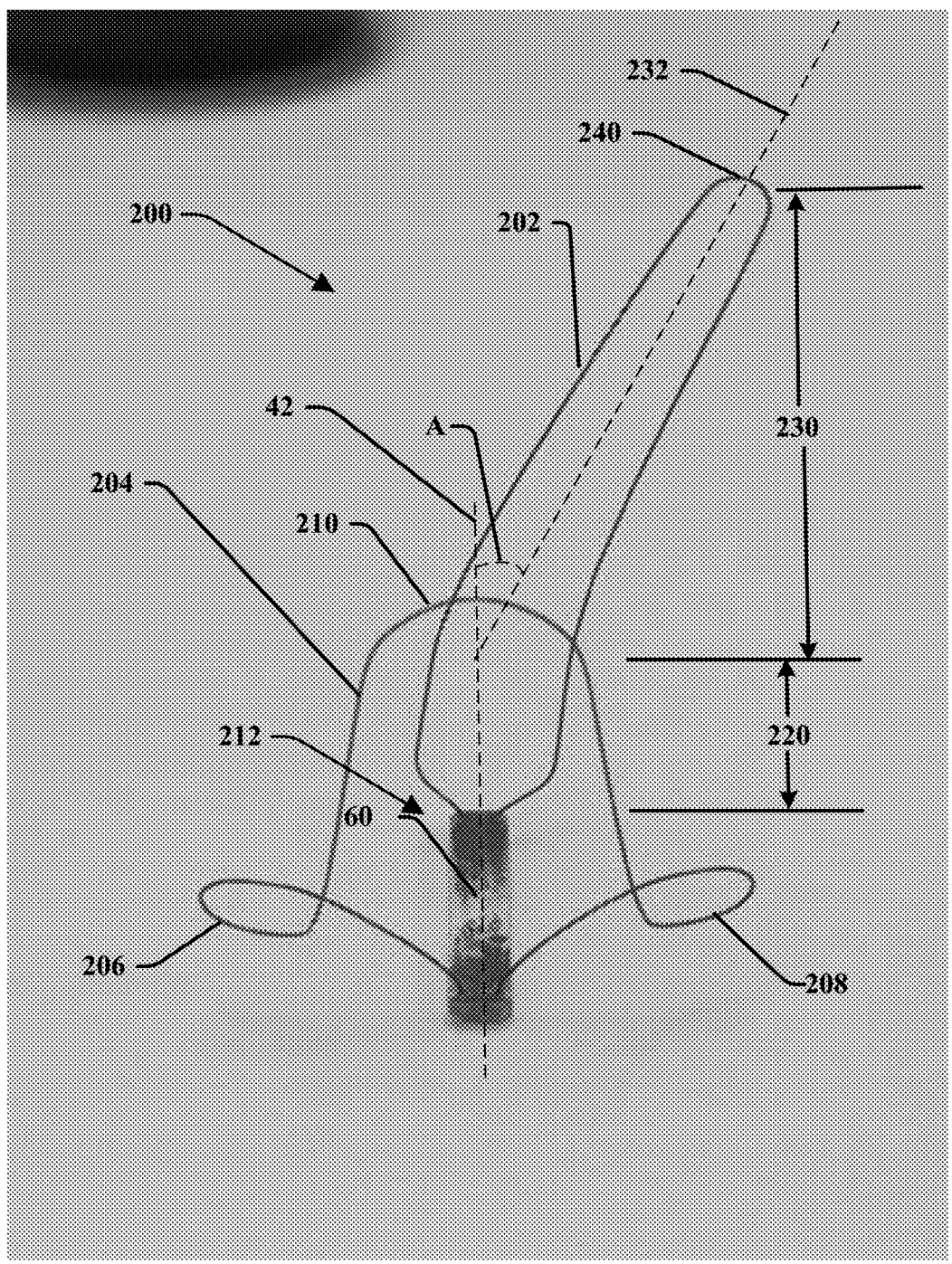
FIG. 5A is an end view of an embodiment of a sensor device or implant with an anchor assembly including a distal anchor having an elongated and angled orientation and a proximal anchor having three lobes in accordance with the present disclosure.
Figure 5B:
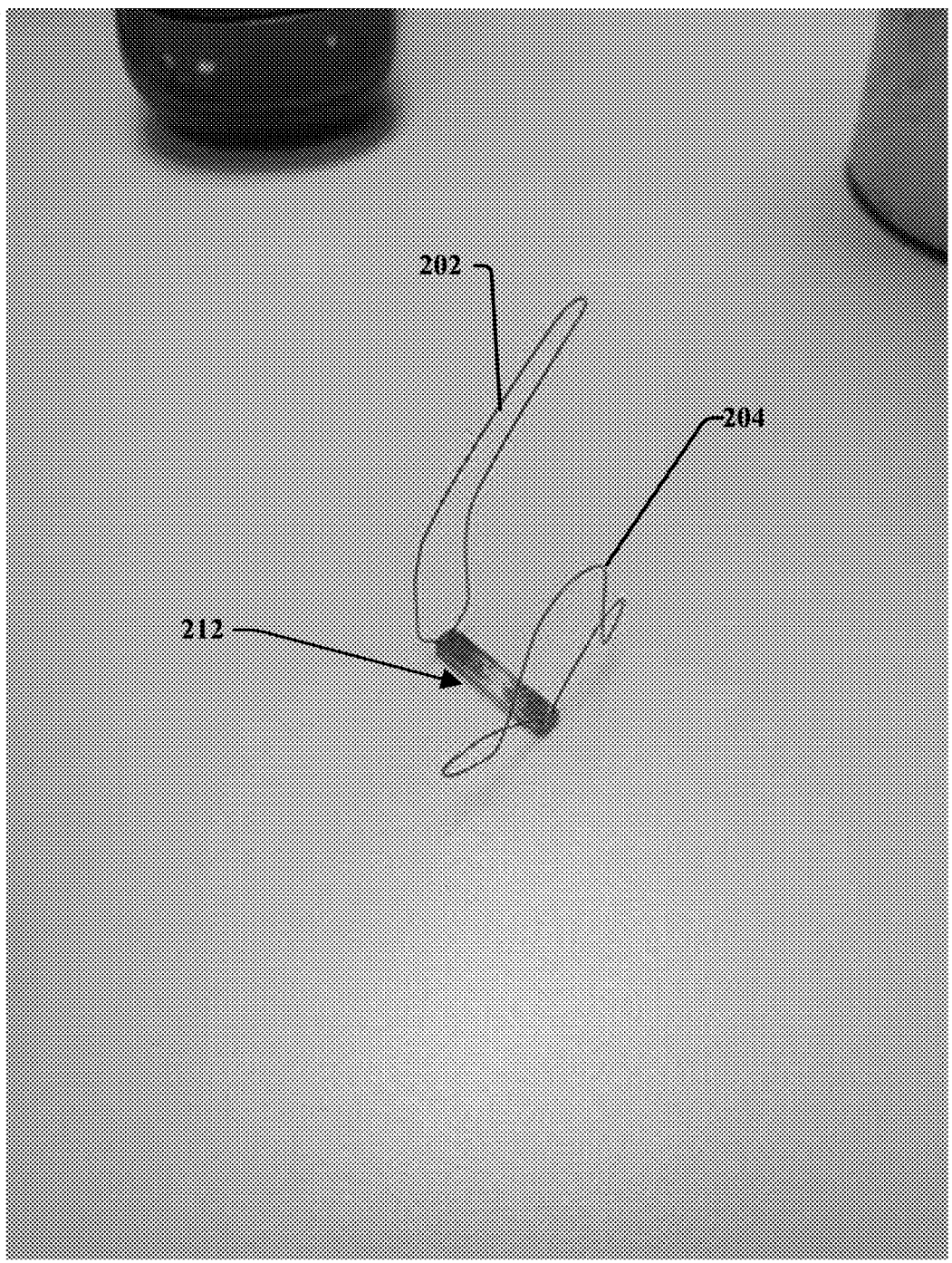
FIG. 5B is a perspective view of the embodiment of the sensor device or implant and anchor assembly of FIG. 5A.
Figure 6A:
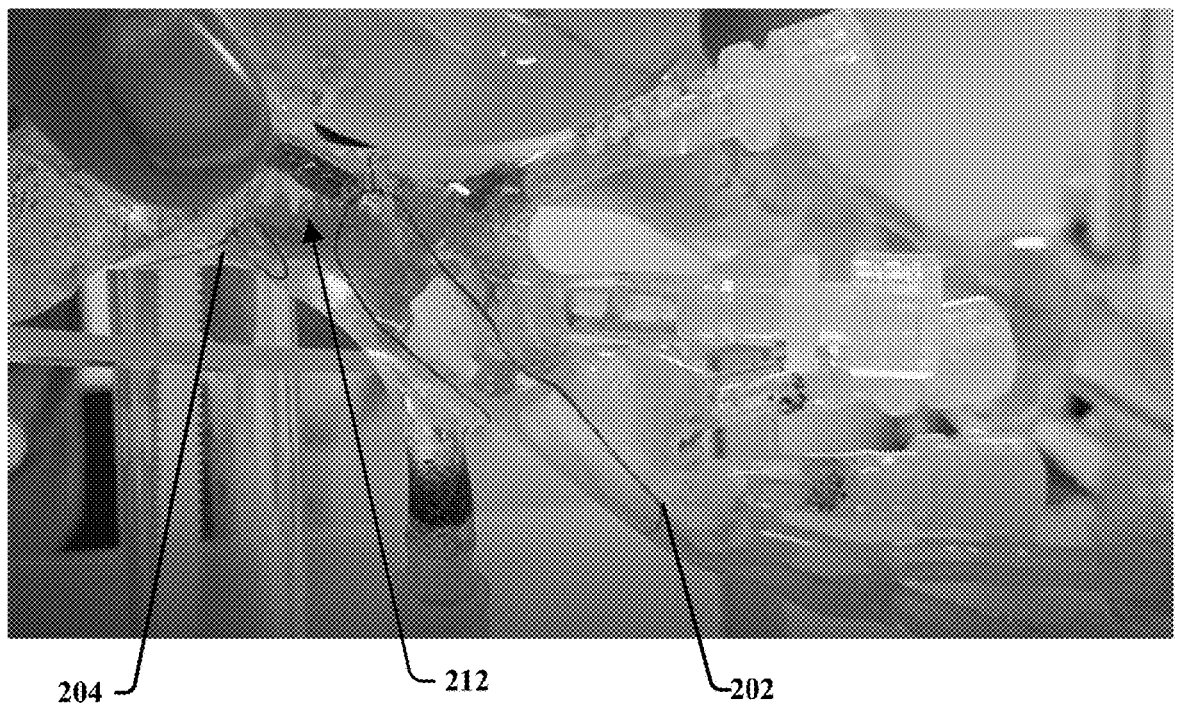
FIG. 6A is a photographic illustration of the a sensor device or implant of FIGS. 5A and 5B positioned within a model of a pulmonary artery.
Figure 6B:
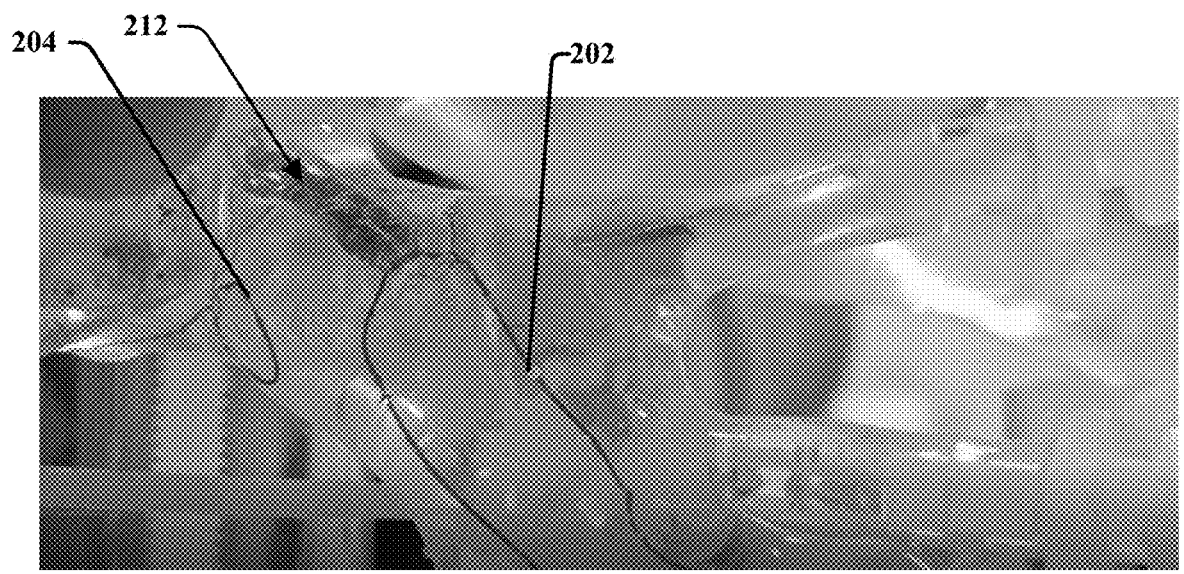
FIG. 6B is a photographic illustration of the a sensor device or implant of FIGS. 5A and 5B positioned within a model of a pulmonary artery.
Figure 7A:
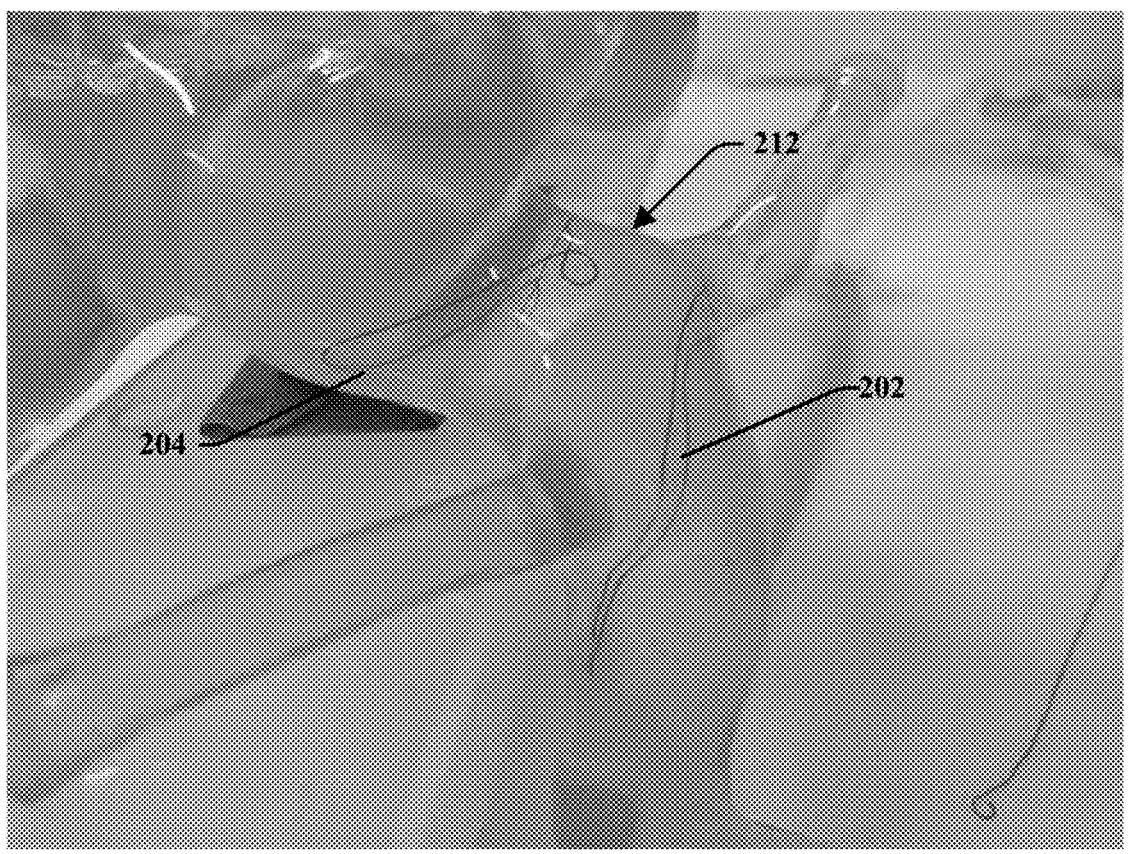
FIG. 7A is a photographic illustration of the a sensor device or implant of FIGS. 5A and 5B positioned within a model of a pulmonary artery.
Figure 7B:
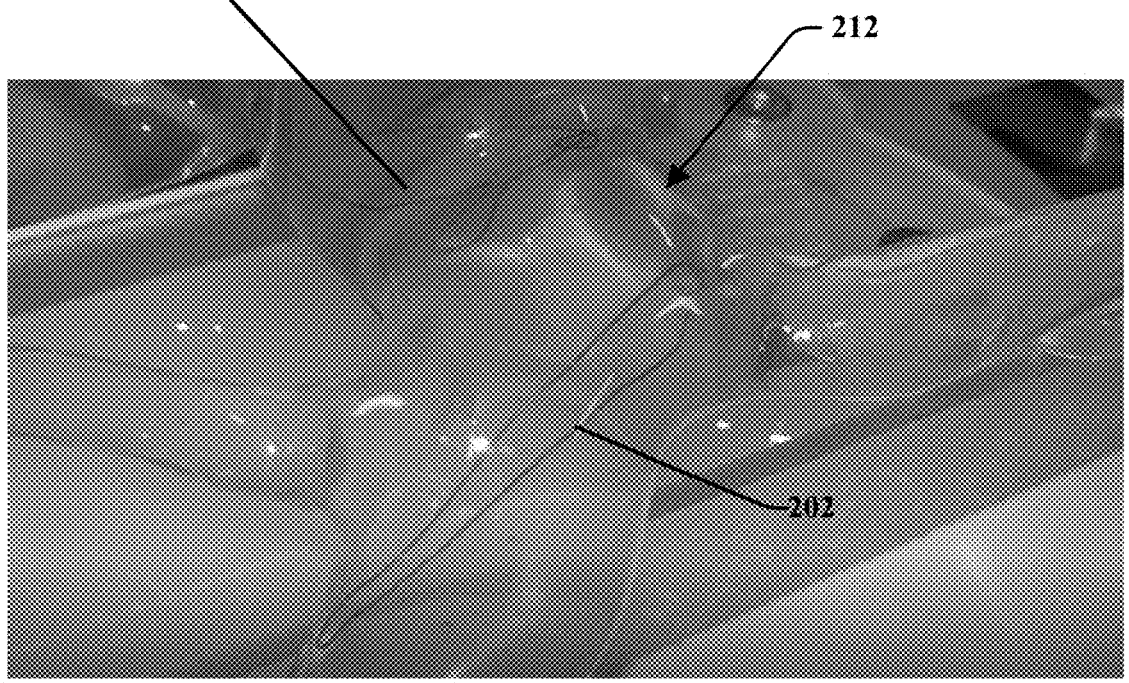
FIG. 7B is a photographic illustration of the a sensor device or implant of FIGS. 5A and 5B positioned within a model of a pulmonary artery.

FIGS. 5A-5B illustrate an embodiment of an anchor assembly 200 with a distal anchoring structure 202 and a proximal anchoring structure 204. The distal anchoring structure includes a wire shaped with an elongated and angled orientation relative to the implant 212. The proximal anchoring structure 204 includes a wire that is shaped as a clover-shaped structure formed by at least smaller two lobes 206 and 208 located on either side of a larger lobe 210. Located in between the distal anchoring structure 202 and the proximal anchoring structure 204 is a suitable implant 212 such as one illustrated by FIG. 1.

The distal anchoring structure 202 and the proximal anchoring structure 204 may extend from a top surface 60 of the implant 212. Notably, the top surface 60 may include a sensor 40 that is attached to an antenna coil within the cavity of the implant housing as illustrated by FIG. 1. Furthermore, the anchoring systems of the present invention may comprise two individual shape set nitinol wires. As illustrated by FIGS. 5A-5B, the two wires comprise a distal wire and a proximal wire, where one anchor wire 202 is attached to the distal portion of a top surface 60 (elongated and angled, see FIGS. 5A-5B) of the implant 212 and the other anchor wire 204 is attached to the proximal portion of the top surface 60 (club shape, see FIGS. 5A-5B). Both anchors 202/204 can be collapsed down and attached to a delivery catheter via "release wires" or other mechanism. The implant 212 and anchors 202/204 can be introduced into the human vasculature in the collapsed position.

In the expanded position, the three-lobed proximal anchor 204 may radially expand to abut the inner wall of the vessel. Lobes 206 and 208 may expand outwardly from the implant 212 while lobe 210 may extend upwardly from the implant 212. These three lobes may radially abut against the inner wall of the vessel and may be arranged to abut against vessels of various sizes. The elongated and angled distal anchor 202 may include a slender configuration that may include a base portion 220 that may extend upwardly and slightly outwardly from the width of the implant 212 and an elongated portion 230 that may extend from the base portion 220 at an angle that includes a gradual taper until it ends at end portion 240. The elongated portion 230 may extend along elongated axis 232 wherein the elongated axis 232 may be positioned angularly relative to the sensor axis 42 as identified in FIG. 5A. The elongated axis 232 may intersect the sensor axis 42 at angle A wherein angle A may be about 20 degrees to about 40 degrees, or more particularly may be about 30 degrees. The elongated portion 230 may be over twice the length of the base portion 220. The slender elongated angle configuration may allow the distal anchor 202 to extend within a branch vessel of the pulmonary artery ("PA") and may correctly position the implant 212 to allow the sensor axis 42 to extend towards the chest of a patient. Further, the configuration of the anchors 202, 204 may be arranged to allow the catheter or other delivery device to deploy the implant 212 with enough room to allow the catheter to be removed without bumping or rubbing against the implant 212 in which it may otherwise move or rotate the implant from its desired position.

Figure 9:
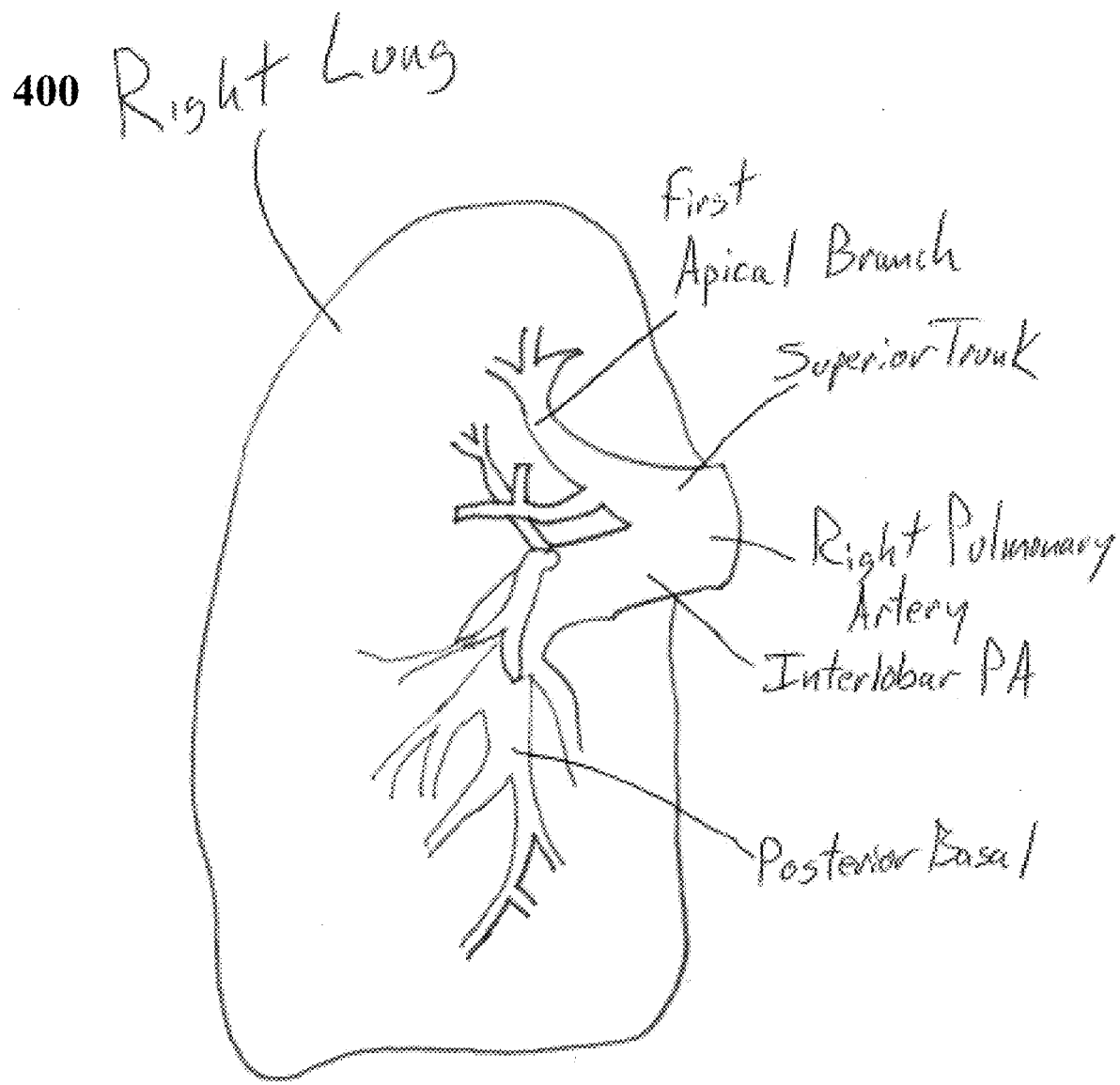
FIG. 9 is a schematic illustration of various arteries of the human anatomy.

It has been found that the elongated and angled configuration of the distal anchoring structure 202 may provide various benefits which may allow health clinicians to deploy the implant at an exact location and orientation with a reduced risk of translation or rotation once deployed. In one embodiment, the implant 212 with the distal anchor 202 may be placed in the right main trunk of the PA. As such, clinicians may be able to position the implant within the PA without having to rely on CT scans or quantitative angiography. Instead, in an embodiment, the clinician may reference the first apical branch of the right main trunk of the PA as an anatomical marker to identify where to position the implant 212 in which the elongated distal anchor 202 may be positioned. FIG. 9 is a labeled sketch of the right pulmonary artery wherein the apical branch is positioned adjacent the superior trunk of the right PA. It should be noted that a wide variety of pulmonary artery anatomy exists between patients. This includes differences in size and number of branches. Despite all this variation, the right PA main trunk has an anatomical feature that is present in nearly all patients in which the clinician may reference for implant placement: a sharp downturn from the right interlobar segment into the right posterior basal segment, see FIG. 9.

The elongated and angled distal anchoring structure 202 may allow the implant 212 to self-correct its position within the vessel. As illustrated by FIGS. 6A-6B and 7A-7B, the distal anchor 202 may be positioned to extend deep into the right posterior basal segment branch of the PA while the proximal anchor 204 may be positioned upstream in the interlobar PA segment. The distal anchor 202 may contact the vessel wall at or near the end portion 240 but it does not need to. Further, it does not need to contact along other radial positions along the base portion 220 or near the base portion 220 along the elongated portion 230, although in some patients it may do so. This may help prevent the implant from translating and rotating and allow the implant to be permanently located therein.

These anchors may allow for ease of implant placement as the distal anchor may be long enough so that when the catheter is removed, there is very little chance of migration into a side branch of the PA. The embodiment may also provide an anatomical landmark facilitating location of the target implant site, that may be easily identified by basic angiography and may allow a health clinician to align the implant such that is just distal from the superior trunk takeoff and proximal to the downturn of the PA. The disclosure may further prevent unwanted rotation due to: the spring force nature of the anchor, delivery system rubbing against the implant during removal, and patient coughing or other patient movement. The angle that the posterior basal makes with respect to the chest skin surface may ensure that the implant assumes an angle towards the chest that is optimal for RF communication. The angle may ensure that the implant faces the chest surface when the distal anchor 202 is placed into the posterior basal segment of the PA.

Further, if there is an unintentional deployment that is too distally positioned in the PA, the distal anchor 202 may still fit within the right posterior basal segment. If there is an unintentional deployment too proximally positioned, the distal anchor 202 may act to "pull" the implant 212 in the distal direction. In the event that the lobes of the proximal anchor 204 may migrate due to the spring force action, the downturn of the distal anchor 202 in the posterior basal segment may prevent it from translating as the elongated distal anchor will be generally prevented from "turning the corner" as the device moves proximally. Further, if there is migration of the implant 212 distally, the housing and distal anchor 202 may form an angle that prohibits them from making the turn. As such, the implant 212 includes self-adjusting properties in this anatomical location within the pulmonary artery.

The two anchors may act to hold the bottom surface 62 of the implant 212 against the vessel wall with the sensor 40 and top surface 60 away from the vessel wall. Because the posterior basal segment is relatively thin, the implant may not sit any other way. The proximal anchor may hold the implant body against the vessel wall by itself without help from the distal anchor 204. The distal anchor may utilize its length relative to the implant to prevent rotation, by staying in the downturn. Additionally, it may prevent unintended interactions with other branches of the PA. The distal anchor 202 may not include loops and may be too straight and long to migrate into side branches easily.

Figure 8:
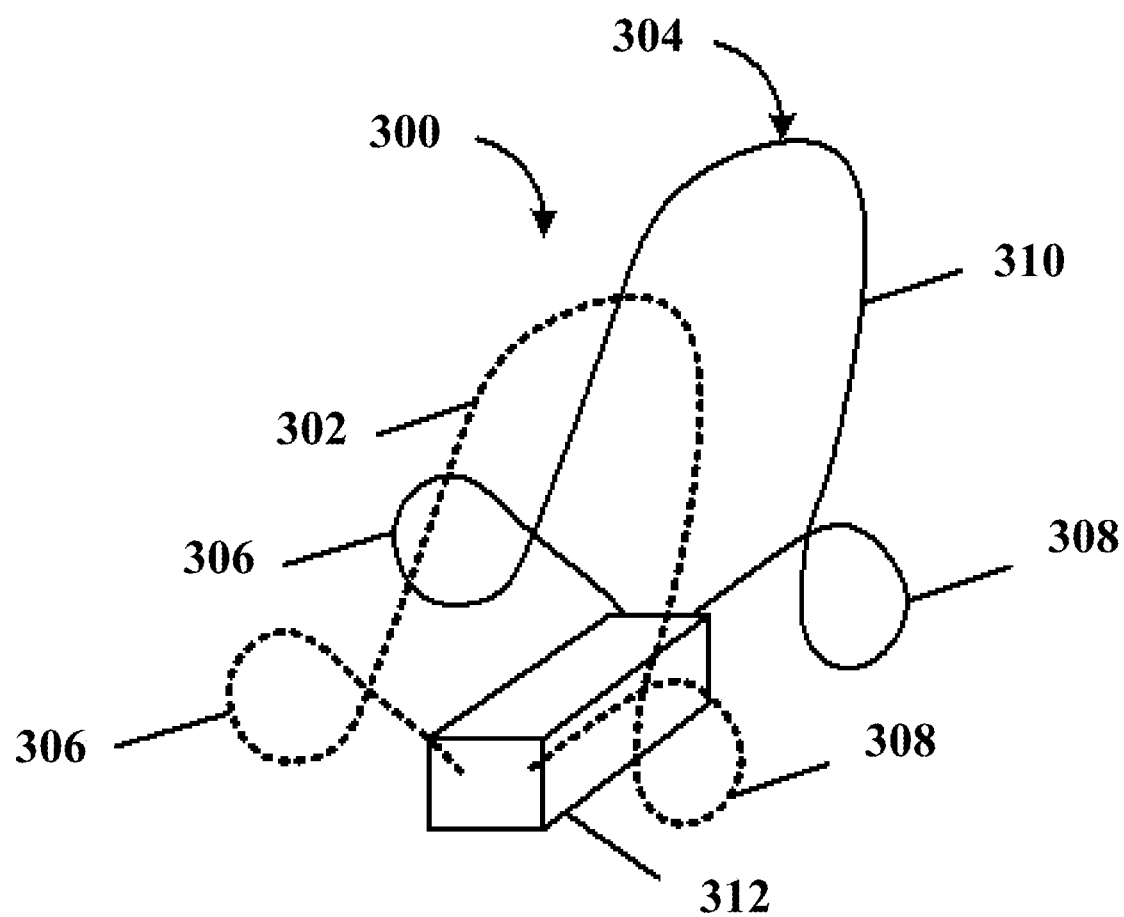
FIG. 8 is a schematic illustration of an embodiment of the present disclosure where a sensor device or implant and an anchoring structure attached thereto are in a state where the anchoring structure is in an expanded state.

In another embodiment as is illustrated in FIG. 8, an anchoring system 300 comprises two anchoring ends, a distal end anchoring structure 302 and a proximal end anchoring structure 304, where both the distal or proximal anchoring structures 302/304 have clover-shaped structures formed by at least two sets of smaller lobes 306 and 308 located on either side of a larger lobe 310. Located in between the distal end anchoring structure 302 and the proximal end anchoring structure 304 is a suitable implant sensor 312.

The anchoring structures of FIGS. 3A-3B, 5A-5B, and 8 are illustrated in the expanded position and it is understood that the anchors may be positioned in a collapsed or retracted position when attached to a catheter or other type of delivery device, such as that shown in FIG. 2. Notably, other anchor configurations and shapes may be implemented, including a different number of anchors (other than two); different locations of anchor attachment to the housing; anchors which attach to the housing at one point, or more than two points; anchors that extend under the housing, around it, or laterally to the sides. The anchors may be formed as loops which anchor the implant to body structures or within a vessel using spring force. The anchors may be made of nitinol, stainless steel, polymer, or any material which is biocompatible and extrudable. The anchors may be made of a combination of materials, such as nitinol with a platinum core. The anchors may be configured to fold down during the implantation procedure to allow easy ingress to the deployment location. The anchors may be configured to be tied down to a delivery system, such as a catheter, for minimally invasive ingress to the implant deployment site. The anchors may be designed to deploy from their tied-down configuration to their open configuration when an operator actuates a control on the proximal end of the delivery system. The control may include release wires that are pulled from the proximal end either directly or with help from a mechanical handle. The anchors may be coated with a material to increase lubricity.

Figure 10:
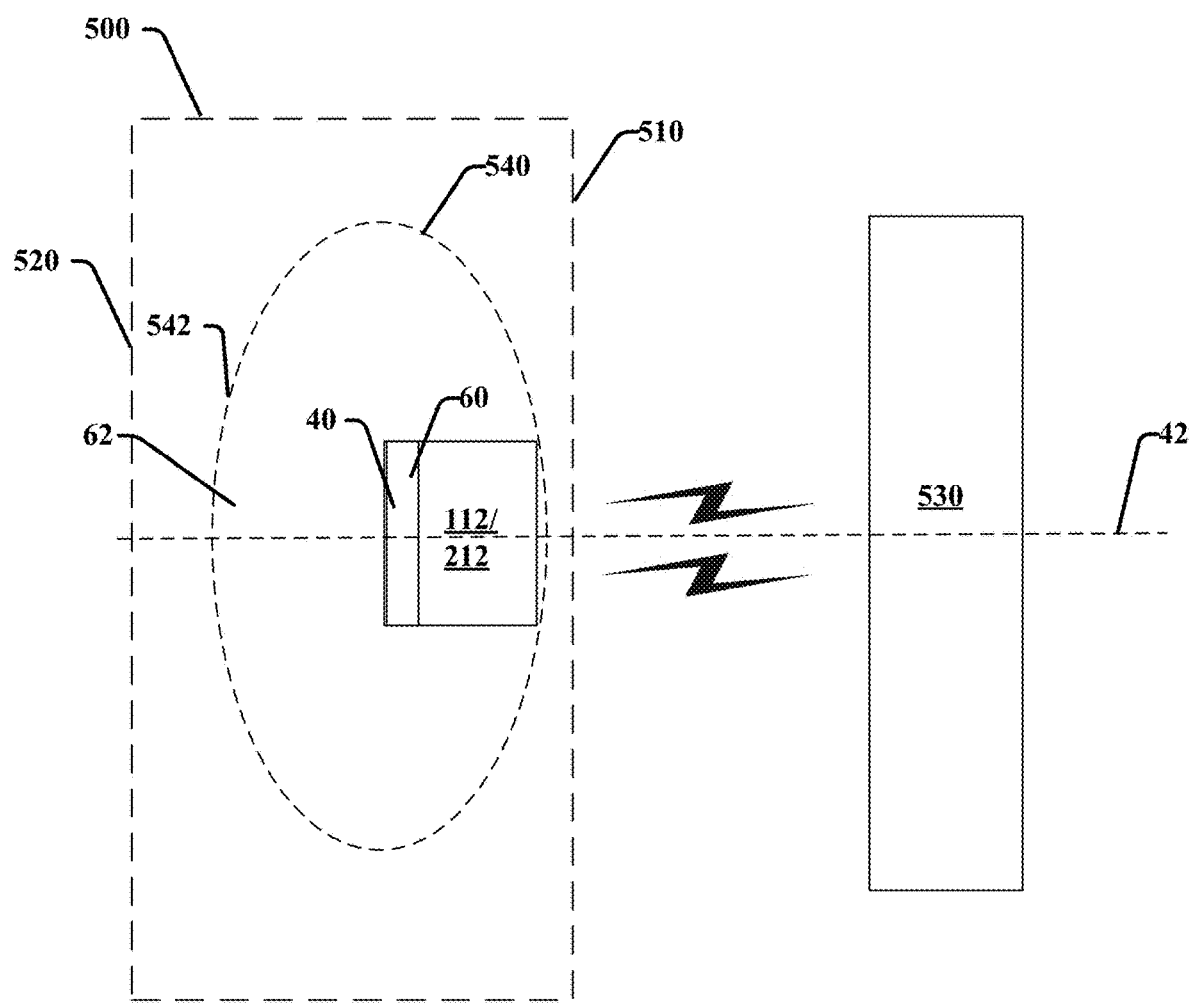
FIG. 10 is a schematic cross-sectional view of a sensor device or implant positioned within the body of a patient and in communication with a reading device.

The anchors may be positioned within the vessel at a desired location and caused to expand in the illustrated expanded positions as illustrated in FIGS. 4, 6A-B, and 7A-B. In these embodiments, as illustrated by FIG. 10, it may be desirable to position the implant 112, 212 within a vessel 540 with the top surface 60 and the sensor 40 aligned along the sensor axis 42 directed through the chest 510 of the patient and wherein the top surface 60 may be spaced from an inner wall 542 of the vessel 540. The configuration of the disclosed anchors may make this position possible as the aligned direction would allow the patient to utilize a reader device 530 to be positioned on or near the chest in proximity to the implant while also being directionally aligned with the top surface 60 and sensor 40. FIG. 10 schematically illustrates a cross sectional view of an implant 112, 212 positioned within a body 500 of a patient wherein the top surface 60 and sensor 40 thereon may be directed towards the center of a blood vessel 540. The implant 112, 212 may be located on the side of vessel 540 such that its distance from the wall of the chest 510, and hence from external reader 530, is minimized. The sensor 40 on the top surface 60 may be aligned along the sensor axis 42 that extends through the chest 510 and a user may allow the reader device 530 to be placed in alignment with the sensor axis 42 to wirelessly communicate with the implant through the chest 510 of the patient. The configuration of the anchor assemblies may allow for the implant to be placed in the desired location, so that a patient having the implant may be able to hold reader device 530 and take his own readings from the implant without the assistance of others. The above embodiment may also be applied to the implant of FIG. 8.

During the deployment of the implant 100/200/300, the anchors 202, 204 may be deployed sequentially when the release wires are retracted. Once an anchor is free and/or fully released, the anchor may utilize nitinol's super elastic property and instantly attempt to return to its initial shape set shape within the vessel. The distal anchor 202 may deploy first, pushing the distal end of the implant straight off the delivery catheter and onto the target position along the vessel wall. Next the proximal anchor 204 may deploy, pushing down the proximal end of the sensor body (the 'implant') 212 along the vessel wall target and engaging the two side lobes. Although stated in terms of implant 200, the above may be applied to any of the embodiments described herein, including implants 100 and 300.

Furthermore, the anchoring systems of the present invention comprise two individual shape set nitinol wires. As discussed above, the two wires comprise a distal wire and a proximal wire, where one anchor wire 102 is attached to the distal end (spade) of the implant 112 and the other anchor wire 104 is attached to the proximal end (club). Both anchors 102/104 can be collapsed down and attached to a delivery catheter via "release wires." The implant sensor 112 and anchors 102/104 can be introduced into the human vasculature through a 14 Fr introducer. The anchors 102/104 are deployed sequentially when the release wires are retracted. Once an anchor is free and/or fully released, the anchor utilizes nitinol's super elastic property and instantly attempts to return to the initial shape set shape within the vessel. The distal anchor deploys first, pushing the distal end of the implant straight off the delivery catheter and onto the target position along the vessel wall. Next the proximal anchor deploys pushing down the proximal end of the sensor body along the vessel wall target and engaging the two side lobes which provide the most radial force and the largest deterrent to proximal migration and rotation. Although stated in terms of implant 100, the above may be applied to any of the embodiments described herein, including implants 200 and 300.

In one embodiment, the overall implant and anchoring structures are sized such that the anchoring system allows the implant to be placed in a proximal segment of the pulmonary artery. The proximal placement allows communication with device to occur from the chest instead of the back. The anchoring system of the present invention is designed to keep maximum vessel contact and remain stable over a large range of vessel sizes as compared to other devices known to those of skill in the art. The anchoring system of the present disclosure is designed to withstand any forces imposed by the retraction of or contact with the delivery catheter which is a well-documented procedure risk for devices designed with anchoring system failing to possess the various physical structures of the present disclosure. For example, if the insertion catheter snags the tip of the proximal anchor, the forces provided by the proximal anchor lobes increases to mitigate proximal movement.

As would be apparent to those of skill in the art, the use of the labels proximal and distal are for convenience sake and could be interchanged such that in the embodiment of FIGS. 3A-B, the distal end of the anchoring system 100 would have the clover-shaped structure formed by at least three lobes 106, 108 and 110. Such a change in orientation could be dictated by the environment and/or blood vessel in which the anchoring system and sensor device of the present disclosure are to be implanted in. The same may be applied to any of the embodiments described herein, including implants in FIGS. 5A-B and FIG. 8.

Regarding the nitinol wires utilized in the embodiments of the present disclosure, such wires are well known in the art and as such a detailed discussion herein is omitted for the sake of brevity. However, as is known to those of skill in the art, nitinol is formed from at least one nitinol alloys, where such alloys exhibit two closely related and unique properties: shape memory effect (SME) and superelasticity (SE; also called pseudoelasticity, PE). Shape memory is the ability of nitinol to undergo deformation at one temperature and then recover its original, un-deformed shape upon heating above its "transformation temperature". Superelasticity occurs at a narrow temperature range just above its transformation temperature; in this case, no heating is necessary to cause the un-deformed shape to recover, and the material exhibits enormous elasticity, some 10 to 30 times that of ordinary metal. Given nitinol's biocompatibility it is well suited for use in biomedical devices and/or implants. Regarding the relationship between smaller lobes 106/108 and 206/208 and larger lobe 110 and 210 of the multi-lobed anchoring structures of the present disclosure, it should be noted that the larger lobe should have an overall length of at least 200 percent the length of the smaller lobes.

While in accordance with the patent statutes the best mode and certain embodiments of the disclosure have been set forth, the scope of the disclosure is not limited thereto, but rather by the scope of the attached. As such, other variants within the spirit and scope of this disclosure are possible and will present themselves to those skilled in the art.

What is claimed is:

1. An anchoring assembly for a vascular implant comprising:
   an implant including an oblong shaped housing that extends along a housing axis;
   at least one anchor attached to said housing, said anchor is an elongated anchor that includes a base portion and an elongated portion wherein said elongated portion extends along an elongated axis, said at least one anchor includes a slender configuration wherein said base portion extends upwardly and outwardly from a width of the implant and wherein said elongated portion extends from the base portion at an angle;
   wherein said at least one anchor is formed from at least one flexible member configured to be placed into a retracted position for catheter delivery, and placed in an expanded position for placement within a vessel;
   wherein said at least one anchor is configured to position said housing against a vessel wall, and;
   wherein said at least one anchor is configured to adapt to at least one anatomical feature of a vessel to prevent movement of said housing, wherein said at least one anatomical feature is a first vessel segment oriented at an angle with respect to an adjoining second vessel segment and wherein said elongated axis of said anchor extends at an angular orientation relative to said housing axis while positioned in said second vessel segment such that the at least one anchor includes self-adjusting properties for the implant positioned in said at least one anatomical feature.

2. The anchoring assembly of claim 1 wherein said at least one anchor is a distal anchor attached to a distal end of said housing.

3. The anchoring assembly of claim 1 wherein said at least one anchor is a proximal anchor attached to a proximal end of said housing.

4. The anchoring assembly of claim 1 comprising two said anchors wherein one said anchor is a proximal anchor attached to a proximal end of said housing and the other said anchor is a distal anchor attached to a distal end of said housing.

5. The anchoring assembly of claim 1 where said at least one anchor is a wire.

6. The anchoring assembly of claim 5 wherein said wire is made from a material consisting of nitinol, stainless steel, platinum, polished nitinol, low-inclusion nitinol, nitinol with a platinum core, or polymer.

7. The anchoring assembly of claim 1 wherein said first vessel segment is the right interlobar pulmonary artery and said second vessel segment is the right posterior basal pulmonary artery.

8. The anchoring assembly of claim 1 wherein said housing is configured to be located in said first vessel segment, and said at least one anchor is configured to extend into said second vessel segment a distance sufficient to prevent translational movement of said implant in at least one direction by impeding movement of the implant about said angle formed by said vessel segments.

9. The anchoring assembly of claim 1 wherein said housing of said implant is configured to be located in said first vessel segment, and said at least one anchor is configured to extend into said second vessel segment a distance sufficient to prevent rotational movement of said implant by inhibiting movement of said implant about said housing axis.

10. The anchoring assembly of claim 1 wherein said housing is configured to be positioned at a location near the surface of the skin.

11. The anchoring assembly of claim 10 wherein said housing is configured to communicate wirelessly with a device positioned outside said vessel containing said implant.

12. The anchoring assembly of claim 1 wherein said assembly is configured to facilitate deployment of said vascular implant at a predetermined location wherein said predetermined location is identifiable by proximity to at least one anatomical feature.

13. The anchoring assembly of claim 12 wherein said at least one anatomical feature is an intersection of the superior apical branch and the interlobar branch of the right pulmonary artery.

14. The anchoring assembly of claim 8 wherein said anchor configured to extend into said second vessel segment is a distal anchor located on the distal portion of said housing.

15. The anchoring assembly of claim 9 wherein said anchor configured to extend into said second vessel segment is a distal anchor located on the distal portion of said housing.

16. The anchoring assembly of claim 14, further comprising a proximal anchor configured to hold said housing against said wall of said vessel.

17. The anchoring assembly of claim 15, further comprising a proximal anchor configured to hold said housing against said wall of said vessel.

18. The anchoring assembly of claim 1 further comprising a second anchor that includes at least three lobe structures arranged in a manner where at least two smaller lobes are located on either side of a larger lobe.

19. The anchoring assembly of claim 1 wherein said implant is a sensor.

20. A method for anchoring an implant inside a blood vessel, comprising the steps of:
attaching at least one flexible anchor to a housing, the housing extends along a housing axis;
collapsing said anchor to a collapsed configuration and attaching said housing to a catheter, wherein said anchor is an elongated anchor that includes a base portion and an elongated portion wherein said elongated portion extends along an elongated axis;
inserting said catheter into a vasculature system and translating said housing to a deployment location;
releasing said housing from the catheter and causing said at least one anchor to expand thereby disconnecting said housing from said catheter, said at least one anchor includes a slender configuration wherein said base portion extends upwardly and outwardly from a width of the implant and wherein said elongated portion extends from the base portion at an angle wherein said anchor positions said housing against a wall of said vessel, further wherein said at least one anchor adapts to at least one anatomical feature to inhibit movement of said housing, wherein said at least one anatomical feature is a first vessel segment oriented at an angle with respect to an adjoining second vessel segment and wherein said elongated axis of said anchor extends at an angular orientation relative to said housing axis while positioned in said second vessel segment such that the at least one anchor includes self-adjusting properties for the implant positioned in said at least one anatomical feature; and
removing said catheter.

21. The method of claim 20 further comprising providing a second anchor that includes at least three lobe structures arranged in a manner where at least two smaller lobes are located on either side of a larger lobe.

22. The method of claim 20, wherein said at least one anchor is formed from a nitinol alloy.

23. The method of claim 20, wherein said housing includes a sensor that is designed for use in a pulmonary artery and said sensor is designed to be read wirelessly from the chest of a patient in which said sensor is implanted.

24. The anchoring assembly of claim 5 wherein said elongated portion includes a gradual taper until it ends at an end portion.

25. The anchoring assembly of claim 1 wherein the elongated axis intersects the housing axis at an angle that is about 20 degrees to about 40 degrees when the anchor is in the expanded position.

26. The method of claim 20 where said at least one anchor includes a slender configuration and wherein said base portion extends upwardly and outwardly from a width of the implant and wherein said elongated portion extends from the base portion at an angle.

27. The method of claim 20 wherein said elongated portion includes a gradual taper until it ends at an end portion.

28. The method of claim 20 wherein the elongated axis intersects the housing axis at an angle that is about 20 degrees to about 40 degrees when the anchor is in the expanded position.

29. An anchoring assembly for a vascular implant comprising:
- an implant including an oblong shaped housing that extends along a housing axis;
- at least one anchor attached to said housing, said anchor is an elongated anchor that includes a base portion and an elongated portion wherein said elongated portion extends along an elongated axis, wherein said elongated portion includes a gradual taper until it ends at an end portion, and wherein the elongated axis intersects the housing axis at an angle that is about 20 degrees to about 40 degrees when the anchor is in the expanded position;
- wherein said at least one anchor is formed from at least one flexible member configured to be placed into a retracted position for catheter delivery, and placed in an expanded position for placement within a vessel;
- wherein said at least one anchor is configured to position said housing against a vessel wall, and;
- wherein said at least one anchor is configured to adapt to at least one anatomical feature of a vessel to prevent movement of said housing, wherein said at least one anatomical feature is a first vessel segment oriented at an angle with respect to an adjoining second vessel segment and wherein said elongated axis of said anchor extends at an angular orientation relative to said housing axis while positioned in said second vessel segment such that the at least one anchor includes self-adjusting properties for the implant positioned in said at least one anatomical feature.

30. The anchoring assembly of claim 1, wherein the elongated portion is over twice the length of the base portion.

* * * * *